US011051749B2

(12) United States Patent
Schalk et al.

(10) Patent No.: US 11,051,749 B2
(45) Date of Patent: Jul. 6, 2021

(54) RAPID MAPPING OF LANGUAGE FUNCTION AND MOTOR FUNCTION WITHOUT SUBJECT PARTICIPATION

(71) Applicants: Health Research, Inc., Menands, NY (US); Albany Medical College, Albany, NY (US)

(72) Inventors: Gerwin Schalk, Glenmont, NY (US); Anthony L. Ritaccio, Voorheesville, NY (US); Adriana De Pesters, Coppet (CH); AmiLyn Taplin, Albany, NY (US)

(73) Assignees: Health Research, Inc., Menands, NY (US); Albany Medical College, Albany, NY (US)

( * ) Notice: Subject to any disclaimer, the term of this patent is extended or adjusted under 35 U.S.C. 154(b) by 917 days.

(21) Appl. No.: 15/570,927

(22) PCT Filed: May 2, 2016

(86) PCT No.: PCT/US2016/030418
§ 371 (c)(1),
(2) Date: Oct. 31, 2017

(87) PCT Pub. No.: WO2016/179094
PCT Pub. Date: Nov. 10, 2016

(65) Prior Publication Data
US 2019/0053734 A1 Feb. 21, 2019

Related U.S. Application Data

(60) Provisional application No. 62/156,237, filed on May 2, 2015, provisional application No. 62/156,422, filed on May 4, 2015.

(51) Int. Cl.
*A61B 5/38* (2021.01)
*A61N 1/36* (2006.01)
(Continued)

(52) U.S. Cl.
CPC .............. *A61B 5/38* (2021.01); *A61B 5/4064* (2013.01); *A61B 5/4094* (2013.01);
(Continued)

(58) Field of Classification Search
CPC ........... A61B 5/369; A61B 5/37; A61B 5/372; A61B 5/374; A61B 5/38; A61B 5/4064; A61B 5/4803
See application file for complete search history.

(56) References Cited

U.S. PATENT DOCUMENTS 8,761,869 B2   6/2014   Leuthardt et al.
8,825,149 B2   9/2014   Kraus et al.
(Continued)

FOREIGN PATENT DOCUMENTS

CA   2048697 A1   2/1992
CN   102429658 A   5/2012
(Continued)

OTHER PUBLICATIONS

Roland, Jarod L et al. "Brain mapping in a patient with congenital blindness—a case for multimodal approaches." Frontiers in human neuroscience vol. 7 431. Jul. 31, 2013, doi:10.3389/fnhum.2013.00431. (Year: 2013).*

(Continued)

*Primary Examiner* — Carrie R Dorna
(74) *Attorney, Agent, or Firm* — Heslin Rothenberg Farley & Mesiti PC

(57) ABSTRACT

Provided is a method for mapping a neural area involved in speech processing, including applying a plurality of recording electrodes to a surface of a cortex of a human subject, presenting a plurality of auditory stimuli to the subject wherein some of the plurality of stimuli are speech sounds and others of the plurality of auditory stimuli are non-speech sounds, recording brain activity during the presenting of the
(Continued)

plurality of auditory stimuli, and identifying one or more brain areas wherein activity changes more after presentation of speech sounds than it does after presentation of non-speech sounds, wherein the human subject does not speak during the presenting and the recording. Also provided is a method for mapping a neural area involved in speech production wherein the human subject does not speak during presenting speech stimuli and recording neural activity.

47 Claims, 18 Drawing Sheets

(51) Int. Cl.
*A61N 1/32* (2006.01)
*A61B 5/00* (2006.01)
*A61N 1/05* (2006.01)
*G16H 20/70* (2018.01)

(52) U.S. Cl.
CPC ............ *A61N 1/0531* (2013.01); *A61N 1/32* (2013.01); *A61N 1/36082* (2013.01); *A61B 2505/05* (2013.01); *G16H 20/70* (2018.01)

(56) References Cited

U.S. PATENT DOCUMENTS

| | | | |
|---|---|---|---|
| 2002/0065580 | A1 | 5/2002 | Derakhshan |
| 2005/0131311 | A1 | 6/2005 | Leuthardt et al. |
| 2005/0182456 | A1 | 8/2005 | Ziobro et al. |
| 2005/0228515 | A1 | 10/2005 | Musallam et al. |
| 2013/0338483 | A1 | 12/2013 | Neuvonen et al. |
| 2015/0313497 | A1* | 11/2015 | Chang .................... A61B 5/377 600/544 |
| 2015/0380009 | A1* | 12/2015 | Chang .................... G10L 15/24 704/263 |

FOREIGN PATENT DOCUMENTS

| | | |
|---|---|---|
| CN | 103054587 A | 4/2013 |
| CN | 103932701 A | 7/2014 |
| WO | 2008008589 A2 | 1/2008 |

OTHER PUBLICATIONS

McCoy et al., "Photosensitisers—the progression from photodynamic therapy to anti-infective surfaces," 2015, 47 pages, Queen's University, Belfast, published in Expert Opinion on Drug Delivery, Copyright 2014.

Safeseries Sil Relays—Overview, 2013/2014, pp. D.2-D.8, Web: www.clrwtr.com, Weidmuller.

Khater et al., "Photoxicity of Rose Bengal against the Camel Tick, *Hyalomma dromedarii*," 2014, pp. 78-86, International Journal of Veterinary Science, vol. 3, No. 2.

Yung et al., "Dengue Serotype-Specific Differences in Clinical Manifestaton, Laboratory Parameters and Risk of Severe Disease in Adults, Singapore," 2014, pp. 999-1005, American Journal Trop. Med. Hyg., vol. 02, No. 5.

Li et al., "Existing drugs as broad-spectrum and potent inhibitors for Zika virus by targeting NS2B-NS3 interaction," 2017, pp. 1-19, Cell Research, www.nature.com/cr.

Boldt et al.; "Listening to an Auto Drama Activates Two Precessing Networks One for All Sounds, ANother Exclusively for Speech," PLOS One, vol. 8, No. 5, May 29, 2013 (May 29, 2013); pp. E64489.

European Search Report mailed in connection with European Patent Application No. 16789892.2 dated Dec. 10, 2018.

European Patent Office Written Opinion mailed in connection with European Patent Application No. 16789892.2 dated Dec. 10, 2018.

Patent Cooperation Treaty, Notification of Transmittal of the International Search Report and the Written Opinion of the International Searching Authority, or the Declaration for PCT/US2016/030418 dated Aug. 8, 2016, 7 pages.

Tamura et al., "Passive language mapping combining real-time oscillation analysis with cortico-cortical evoked potentials for awake craniotomy," Mar. 2016, pp. 1-9, AANS, Journal Neurosurg.

Taplin et al., "Intraoperative Mapping of Expressive Language Cortex Using Passive Real-Time Electrocorticography," Mar. 2016, 18 pages, Epilepsy & Behavior Case Reports.

De Pesters et al., "Electrocorticographic mapping of expressive language function without requiring the patient to speak: A report of three cases," Feb. 2016, 19 pages, Epilepsy & Behavior Case Reports.

Brunner et al., "A Practical Procedure for Real-Time Functional Mapping of Eloquent Cortex Using Electrocorticographic Signals in Humans," Jul. 2009,, pp. 278-286, Epilepsy Behavior, vol. 15, No. 3, NIH Public Access.

Kunieda et al., Intraoperative Dorsal Language Network Mapping by Using Single-Pulse Electrical Stimulation, Sep. 2014, 18 pages, ResearchGate, Article in Human Brain Mapping.

Breshears et al., "Electrocorticographic Frequency Alteration Mapping of Speech Cortex during an Awake Craniotomy: Case Report," Nov. 2009, pp. 11-15, Stereotactic and Functional Neurosurgery, Technical Report.

Su et al., "Electrocorticographic Sensorimotor Mapping," Jun. 2013, pp. 1-10, Clin. Neurophysiol. vol. 126, No. 6, NIH Public Access.

Saito et al., "Intraoperative cortico-cortical evoked potentials for the evaluation of language function during brain tumor resection: initial experience with 13 cases," 2014, pp. 827-838, J. Neurosurg, vol. 121.

Roland et al., Passive real-time identification of speech and motor cortex during an awake craniotomy, 2010, pp. 123-128, ScienceDirect, Epilepsy and Behavior, vol. 18.

Genetti et al., "Comparison of high gamma electrocorticography and fMRI with electrocortical stimulation for localization of somatosensory and language cortex," 2015, pp. 121-130, ScienceDirect, Clinical Neurophysiology vol. 126.

Chinese Office Action (and English translation) issued for Chinese Patent Application No. 201680039270.0 dated Feb. 3, 2020.

* cited by examiner

RAPID MAPPING OF LANGUAGE FUNCTION AND MOTOR FUNCTION WITHOUT SUBJECT PARTICIPATION

CROSS-REFERENCE TO RELATED APPLICATIONS

This application is a national stage filing under section 371 of International Application No. PCT/US2016/0030418 filed May 2, 2016, published in English on Nov. 10, 2016 as WO2016/179094A1, which claims priority under 35 U.S.C. § 119 to U.S. Provisional Application No. 62/156,237, filed May 2, 2015, which is herein incorporated by reference in its entirety, and U.S. Provisional Application No. 62/156,422, filed May 4, 2015, which is herein incorporated by reference in its entirety.

GOVERNMENT RIGHTS STATEMENT

This invention was made with government support under EB000856 and EB018783 awarded by the NIH, and W911NF1410440 awarded by the ARMY/ARO. The government has certain rights in the invention.

FIELD OF THE INVENTION

The present invention relates to, inter alia, rapid mapping of language function and motor function without subject participation.

BACKGROUND OF THE INVENTION

Mapping areas of individuals' brains that are responsible for processing language, sensory, motor, or other functions can be done by measuring brain waves and asking subjects to participate in various tasks, such as those related to linguistic or motor functions. Neural activity elicited by presentation of sensory stimuli, such as tactile or auditory, also signify brain regions involved in processing such stimuli and/or producing behavioral responses thereto. However, currently available methodologies for such mapping are hampered by various limitations, such as the need for subject responsiveness during mapping. For example, electrical cortical stimulation, a widely used measure for brain mapping, conventionally works by assessing the effect of electrical stimulation (ECS) of distinct brain regions on a subject's behavior, where effects of stimulation indicates that the stimulated region plays a function in such behavior. For certain behaviors and subjects, however, ECS is not useful as a brain mapping technique, such as where subjects may be incapable of or poor at the given behavior at baseline (e.g., speech and aphasic subjects, or musculoskeletal responses in paralyzed subjects). ECS also poses risks, including the unintentional induction of seizures.

Functional language or sensorimotor mapping for perioperative planning, such as with regard to surgical removal of brain tumors or epileptogenic neural tissue, is of utmost importance given the high variability in structural anatomy and function across individuals. For example, structurally, essential language cortex can occupy from 1 cm² to greater than 6 cm². Functionally, classical Wernicke's region, considered important for processing and interpreting received language stimuli, varies substantially, since it is the highest common receptive language node in only 36% of people. Similarly, only 79% of people have a classically defined Broca's area, which is considered to be responsible for initiating and controlling the expression of language. Broca's area (expressive language) consists of the pars triangularis and pars opercularis of the inferior frontal gyms, while Wernicke's area (receptive language) encompasses a region of the posterior superior temporal gyms. The two regions are connected through the arcuate fasciculus, likely with involvement of other white matter tracts. In order to avoid inadvertent interference with language or sensorimotor functions by surgical resection of brain tissue responsible for controlling these functions, it is therefore necessary to map, for the individual patient, precisely what region or regions of the cortex are responsible for controlling them such that they can be avoided during resection or other procedures. There is therefore a need for an improved method for mapping neural regions responsible for particular functions, such as language or sensorimotor function.

SUMMARY OF THE INVENTION

The present invention relates to, inter alia, a method for mapping a neural area involved in speech processing, including applying a plurality of recording electrodes to a surface of a cortex of a human subject, presenting a plurality of auditory stimuli to the subject wherein some of the plurality of stimuli are speech sounds and others of the plurality of auditory stimuli are non-speech sounds, recording brain activity during the presenting of the plurality of auditory stimuli, and identifying one or more brain areas wherein brain activity of the one or more brain areas changes more after presentation of speech sounds than it does after presentation of non-speech sounds, wherein the human subject does not speak during the presenting and the recording.

In another aspect, the present invention relates to, inter alia, a method for mapping a neural area involved in speech production including applying a plurality of recording electrodes to a surface of a cortex of a human subject, presenting a plurality of auditory stimuli to the subject wherein some of the plurality of stimuli are speech sounds and others of the plurality of auditory stimuli are non-speech sounds, recording brain activity during the presenting of the plurality of auditory stimuli, and identifying one or more brain areas wherein brain activity of the one or more brain areas changes more after presentation of speech sounds than it does after presentation of non-speech sounds, wherein the human subject does not speak during the presenting and the recording.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements. The foregoing and other objects, features, and advantages of the invention are apparent from the following detailed description taken in conjunction with the accompanying drawings in which.

DETAILED DESCRIPTION OF THE INVENTION

Figure 1:
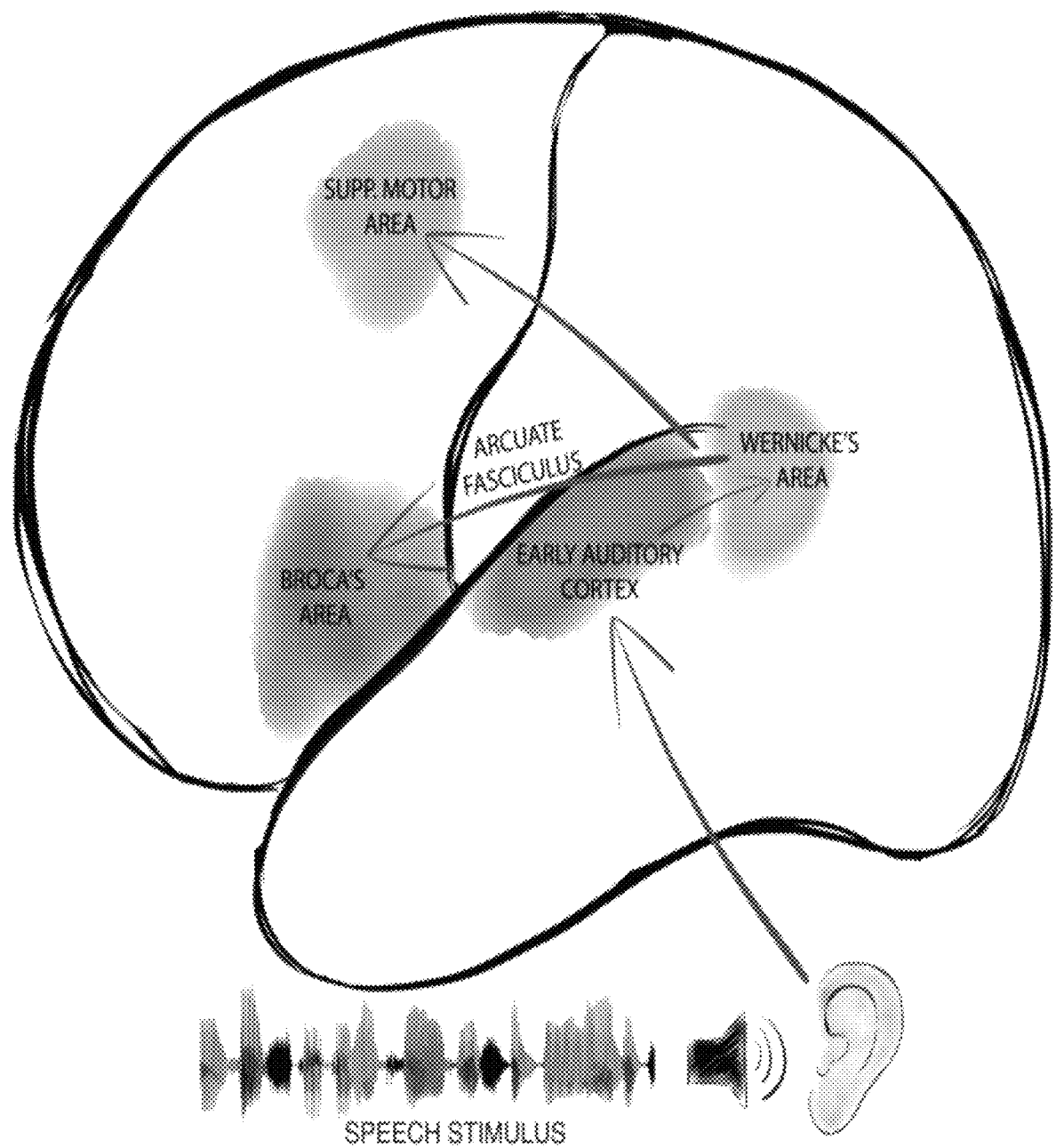
FIG. 1 is a schematic diagram of major cortical regions involved in language processing, and major pathways between them.

Aspects of the present invention and certain features, advantages, and details thereof, are explained more fully below with reference to the non-limiting embodiments illustrated in the accompanying drawings. Descriptions of well-known materials, fabrication tools, processing techniques, etc., are omitted so as to not unnecessarily obscure the invention in detail. It should be understood, however, that the detailed description and the specific examples, while indicating embodiments of the invention, are given by way of illustration only, and are not by way of limitation. Various substitutions, modifications, additions and/or arrangements within the spirit and/or scope of the underlying inventive concepts will be apparent to those skilled in the art from this disclosure.

The present invention relates to, inter alia, methods, devices, and systems for mapping areas of the brain responsible for various functions, such as receptive language functions (i.e., receiving, perceiving, interpreting, and/or understanding verbal communication such as spoken words), expressive language or language production (e.g., creating and/or producing verbal language such as orally), and sensorimotor processing (e.g., sensing and perceiving tactile stimulation and causing movement of a part or parts of the body). There are various methodologies currently available for detecting activity in regions of the brain in response to presentation of various modalities and/or cognitive or behavioral responsiveness to stimuli including commands or instructions. Among the most sensitive and accurate is ECoG, which entails placement of recording electrodes on the surface of the brain. Herein, ECoG and describing placement of electrodes on the brain includes both subdural placement of electrodes, where electrodes are placed directly on the surface of the brain (i.e., the dura mater is not between an electrode and the surface of the brain) and epidural placement of electrodes (i.e., electrodes are placed on the dura mater such that the dura is between an electrode and the surface of the brain). Brain waves across a full spectrum of frequencies, including from approximately 0.5-4 Hz (delta waves), to approximately 4-8 Hz (theta waves), to approximately 8-12 Hz (alpha waves), to approximately 12-40 Hz (beta waves), to above approximately 40 Hz (gamma waves).

As opposed to fMRI or ECS, ECoG does not require electrical stimulation of the brain, permits measurement of neural activity in real time, can be employed in a surgical theater without the need for an fMRI machine, and does not carry a risk of stimulation-induced seizure. An array of recording electrodes may be placed over a region generally known or believed to play a role in a certain function, the performance of the function by the subject elicited (be the function involved in reception of stimuli, interpretation of language, cognitive ability, or behavioral or language production). By observing brain waves detected by the electrodes and determining changes in activity detected by different electrodes during a time frame corresponding to the elicitation of function (e.g., during a period of exposure to speech sounds or tactile stimuli), specific locations of the brain responsible for such functions can be identified and distinguished from uninvolved regions with a high degree of spatial resolution.

For certain functions, however, it has conventionally been difficult to use ECoG or other mapping techniques to map the brain in certain circumstances, such as with particular subjects and particular functions. One such example is language mapping during surgery. For example, it is sometimes necessary to remove a tumor or epileptogenic region from the brain surgically. Preferably, a surgeon should avoid damaging brain regions responsible for particular functions (such as language, or sensorimotor functioning) if possible when resecting a tumor or other diseased or disease-inducing tissue, lest these functions become temporarily or permanently impaired by the surgery. However, given the inter-individual heterogeneity of localization of certain functions, determining precise neural localizations of functions is difficult or impossible if based solely on the visual inspection of landmarks visible on the surface of the brain, it is difficult or impossible to know without performing brain mapping what specific regions are responsible for these functions in a given subject.

In accordance with an embodiment of the improvements disclosed herein, rapid mapping of language function and motor function in the brain of a subject may be performed. More particularly, rapid mapping can be performed passively, in that the mapping does not require active participation from the subject. Therefore, the systems and methods of the present invention provide a means for conducting brain mapping of a subject before and/or during brain surgery in order to identify areas of a brain that relate to either language function or motor function. Such information can be conducted without requiring the subject to actively respond to stimuli to trigger language or motor functional responses. This information can be important for a surgeon conducting brain surgery (e.g., brain tumor removal or epileptogenic tissue removal), as language and motor function are two of the most important functions that a surgeon would want to leave intact post-surgery. As such, the present invention provides systems and methods to aid in brain surgery. As used herein, "motor function" also includes "sensory function." Other aspects of the present invention are further described herein.

In one aspect of the invention, improved mapping of anesthetized subjects (i.e., subjects who are under the influence of anesthesia, such as intraoperatively, during a period of neural mapping) is provided. However, the invention applies equally well to neural mapping of subjects who are non-responsive for reasons other than anesthesia-induced unconsciousness, who are conscious but incapable of providing oral or other sensorimotor responses, or who are awake and capable of responding but for particular reasons elicitation of such responsiveness is undesirable for a given application. In one aspect, the present invention provides a method for rapid mapping of language function of a subject, said method comprising steps as disclosed and/or contemplated herein.

In one embodiment of this method, mapping may be performed without active participation from the subject. In another embodiment, mapping may be performed before and/or during a brain surgical procedure being conducted on a subject. In a further embodiment, mapping may inform a surgeon or medical practitioner conducting a brain surgical procedure of regions of a subject's brain relating to language function. In another embodiment, mapping may involve use of electrodes applied to a subject's brain. In another embodiment, mapping may involve use of electrodes applied to a subject's brain and a computer for providing output with respect to language function. In a further aspect, provided is a system for rapid mapping of language function of a subject, said system comprising aspects, devices, and/or apparatuses as disclosed and/or contemplated herein.

In one embodiment, a system is provided in which aspects, devices, and/or apparatuses of the system may enable mapping to be performed without active participation from a subject. In another embodiment, a system is provided wherein aspects, devices, and/or apparatuses of the system enable mapping to be performed before and/or during a brain surgical procedure being conducted on a subject. In a further embodiment aspects, devices, and/or apparatuses of a system enable mapping to inform a surgeon or medical practitioner conducting a brain surgical procedure of regions of a subject's brain relating to language function. In another embodiment, aspects, devices, and/or apparatuses of a system include electrodes applied to a subject's brain. In another embodiment, aspects, devices, and/or apparatuses of a system include electrodes applied to a subject's brain and a computer for providing output with respect to language function.

In another aspect, provided is a method for rapid mapping of motor function of a subject, said method comprising steps as disclosed and/or contemplated herein. In one embodiment, mapping may be performed without active participation from a subject. In another embodiment, the mapping may be performed before and/or during a brain surgical procedure being conducted on a subject. In a further embodiment, mapping informs a surgeon or medical practitioner conducting a brain surgical procedure of regions of the brain of a subject relating to motor function. In an embodiment, mapping involves use of electrodes applied to a subject's brain. In a further embodiment, mapping involves use of electrodes applied to a subject's brain and a computer for providing output with respect to motor function.

In another aspect, provided is a system for rapid mapping of motor function of a subject. In an embodiment, aspects, devices, and/or apparatuses of a system enable mapping to be performed without active participation from a subject. In another embodiment, aspects, devices, and/or apparatuses of a system enable mapping to be performed before and/or during a brain surgical procedure being conducted on a subject. In a further embodiment, aspects, devices, and/or apparatuses enable mapping to inform a surgeon or medical practitioner conducting a brain surgical procedure of regions of the brain of a subject relating to motor function. In another embodiment, aspects, devices, and/or apparatuses of a system include electrodes applied to a subject's brain. In another embodiment, the aspects, devices, and/or apparatuses of a system include electrodes applied to a subject's brain and a computer for providing output with respect to motor function.

Provided is a method for identifying neural areas responsible for language and/or sensorimotor function without requiring participation of a subject. As disclosed herein, a method allows for identifying neural regions responsible for receptive language functions (for example, within Wernicke's area), expressive language functions (for example, within Broca's area), and/or different portions of sensory and/or motor cortex responsible for specific body regions. Surprisingly, and in contrast to conventional techniques and literature, a method is provided for mapping receptive and expressive language functions in subjects without requiring their participation, including if they are unconscious, such as if they are under the influence of surgical anesthesia at the time brain mapping of such functions is performed. Such method is real-time, allows rapid mapping, and can be performed during a same surgical procedure during which other surgical procedures, such as a resection, are performed, in the same surgical suite, and after a subject has been anesthetized without requiring bringing them out of anesthesia for mapping.

Shown in FIG. 1 are several brain regions involved in language processing, including early auditory cortex, and receptive language function. Some of these regions show changes in neural activity upon exposure to auditory stimuli generally, such as early auditory cortex. Others, such as those involved in receptive language function (e.g., Wernicke's area) preferentially respond to speech and speech-like sounds compared to non-speech sounds. Receptive language areas may show an alteration in activity throughout the duration of presentation of a speech stimulus. Other areas, such as expressive speech (e.g., Broca's area) may be particularly active during production of speech. As disclosed herein, at certain time points during presentation of speech or speech-like sounds, expressive areas preferentially show alterations of activity in response to presentation of speech or speech-like sounds compared to presentation of non-speech-like sounds, even when a subject is not producing speech in response to receipt of the speech stimulus. Furthermore, such responses are detectable in anesthetized subjects, enabling real-time brain mapping during surgery without requiring awakening a patient.

In one aspect, recording electrodes are placed on exposed cortex, including in a region generally predicted to be early auditory cortex, receptive language, and/or expressive language in function, and auditory stimuli are presented. Some auditory stimuli consist of speech sounds, whereas others are scrambled speech possessing acoustic characteristics of speech but not consisting of words (i.e., scrambled speech). Such auditory stimuli are presented to a subject and brain waves, such as broadband gamma waves, are recorded. Production of speech or other behavioral responsiveness to speech or other auditory stimulation are not required of the patient. Alterations in neural activity detected by an electrode during presentation of speech stimuli, wherein such alterations are not seen or are demonstrably diminished in response to presentation of non-speech or scrambled speech sounds, signify that the brain region from which the electrode records brain activity is involved in speech processing, particularly if the electrode has been placed in the general region where receptive and expressive language functions are known to be effectuated.

Brain wave impulses detected by an electrode may be passed through a filter, rendered digitally by a computer or processor, and transformed into stimuli perceptible to a physician or other medical care provider or other trained personnel with skill the field of brain mapping according to known methodology. Such individual may observe neural activity rendered by such a system to identify regions recorded by electrodes evincing changes in activity in response to speech stimuli, including differential responsiveness to speech and non-speech stimuli. An electrode whose trace recording demonstrates such differential responsiveness signifies where speech function may be processed neurally.

A processor or computer may also may be used to control and/or record the time of stimulus onset and the time of stimulus cessation, and provide an indication of such initiation, cessation, and duration of stimulus presentation, as well as what type of stimulation (speech or non-speech) is presented, concurrently with the perceptible rendering of neural activity. In such manner, a skilled person would be enabled to compare whether and how much neural activity changes in a given region, and in response to what type of stimulus, to the presence of speech and non-speech stimuli. For example, a visual trace may be presented of activity detected by an electrode when no stimulation is presented, another when a non-speech auditory stimulus is presented (e.g., optionally, scrambled speech), and another when a speech stimulus is presented, with all three traces superimposed over each other, synchronized (for the non-speech- and speech-related traces) around when presentation of an auditory stimulus was initiated (or terminated, or any particular time point or sampling period after initiation or termination as may be desired or advantageous for mapping particular functions). Such method would permit comparison of how a region compared in response to different stimuli.

A computer or processor may further store instructions for screening responses detected from an electrode. For example, a processor may contain processing instructions for comparing a filtered digitized trace against a threshold level of change in activity that signifies activation, either absolutely or when sampled at an advantageous time point or period of time with respect to an onset or termination of an auditory stimulus. Such processor could also screen for differences in responsiveness detected by an electrode to speech and non-speech stimulus. In this way, a system in accordance with the present disclosure may support automated detection of a brain region that may activated by presentation of speech stimuli (i.e., shows a change in activity above baseline that exceeds a minimum threshold predetermined to characterize a responsive region), that may specifically be involved in speech processing (i.e., shows such change in response to speech sounds but not non-speech sounds, or shows a difference in responsiveness to such sounds that exceeds a particular threshold that signifies differential responsiveness), and/or shows any of the above throughout the duration of presentation of a speech sound or only at specific intervals or periods (e.g., during a pre-specified window following initiation of speech sound presentation or cessation thereof).

Multiple electrodes may be placed on a subject's brain and recorded from simultaneously. For example, arrays of pluralities of electrodes may be placed over a brain region or regions and recorded from simultaneously. During a surgical procedure, time may be extremely limited and rapid processing of information may be essential for a successful operation and health of and recovery by a patient. Use of arrays of pluralities of electrodes exponentially increases the amount of information and the number of brain regions that can be sampled in a given time frame and expedites identification of brain regions responsible for particular functions. In addition, simultaneous computer processing of wave traces from multiple electrodes enables a rapidity of analysis that may not be possible absent such processor and may not be feasible without such processor depending on the time pressures attendant a given procedure. For example, a processor could automatically screen input from an array of 64 electrodes, or multiple such arrays, and signify a smaller number for attention by a skilled practitioner, obviating the need for scrutiny of traces recorded by every electrode.

Some language processing areas may respond throughout one, two, or more seconds of presentation of speech stimuli. For example, a receptive speech area (e.g., Wernicke's) may respond for however so long a speech stimulus is presented. Other areas responsible for speech processing, such as expressive speech areas (e.g., Broca's area), may show altered responsiveness only during a limited portion of time during which a speech stimulus is presented. As one, non-limiting example, an electrode placed over Broca's area may detect a change in activity during between 250 ms and 740 ms after onset of a speech stimulus even though the speech stimulus may continue to be presented following this time period. Or, such change may be detected during between 100 ms and 1000 ms after stimulus onset, 10 ms to 250 ms after stimulus onset, 750 ms and 1000 ms after stimulus onset, 300 ms or 800 ms after stimulus onset, or between 100 ms and 1000 ms after onset of speech stimulus presentation, or some other time-delimited period during but not coextensive with the period during which a speech stimulus is presented. All of the foregoing may characterize responsiveness of electrodes on the brain of a subject who is under anesthesia throughout the entire period or stimulus presentation and response recordation. Such changes in responsiveness could be broadband gamma activity, but theta, delta, alpha, or beta activity may also be observed and indicative of altered responsiveness to stimulation.

Any size of electrode and inter-electrode spacing, or size or shape of electrode array may be used in accordance with the present disclosure. Electrodes may have an exposed surface, for measuring neural activity, of approximately 1 mm or less, or between approximately 1 mm and approximately 2.5 mm, or between approximately 2.5 mm and 5 mm, or larger. They may be spaced from each other by approximately 5 cm or less, 2.5 cm or less, 1 cm or less, 500 mm or less, 100 mm or less, 10 mm or less, 5 mm or less, or 3 mm or less, approximately.

EXAMPLES

In one example, patients passively listened to 32 words and 32 non-words while awake and under anesthesia and neural activity was measured via ECoG. A minimum of 4 runs for each condition (at least 128 words and 128 non-words) were presented. The auditory stimuli consisted of 32 words and 32 unintelligible non-words, i.e. sounds that match the words in duration, intensity, temporal modulation, and power spectrum but are not intelligible. See Canolty et al. (2007) Frontiers in Neuroscience, 1:14. Both types of stimuli activate the primary auditory cortex. A block consisted of a 20 s baseline followed by the 64 stimuli randomly interleaved. Each block had a duration of approximately 2 min. The sounds were presented via earphones placed in the ears of the patient during the surgical prepping. Two blocks were presented while the patient is still awake and used as a control for the coverage of Wernicke's area. A minimum of four blocks were then presented following the sedation of the patient with propofol. A general predicted vicinity of Wernicke's area was located using known methodology, including visualizing landmarks on the brain surface as is well-known in the field. We locations corresponding to Wernicke's area were stimulated to induce cortico-cortical evoked potentials (CCEPs) in Broca's area using well-known protocols. See Matsumoto et al. (2004) Brain, 127: 2316-30. A minimum of 50 CCEPs was determined for each location, over less than 1 minute for each location with a stimulation frequency of 2 Hz.

Figure 2A:
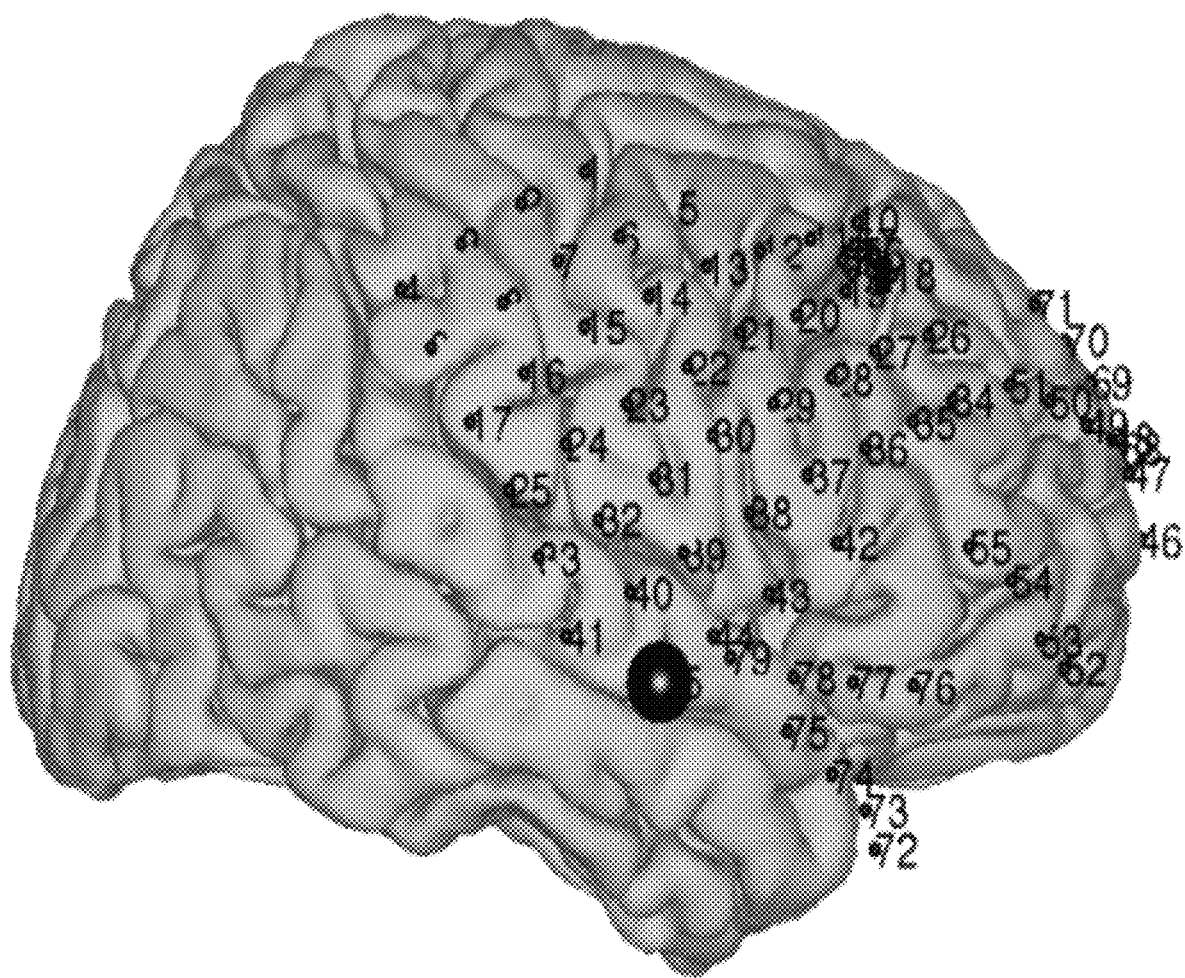
FIG. 2A is a topographical mapping showing placement of recording electrodes in a subject whose neural activity while the subject was awake was recorded.
Figure 2B:
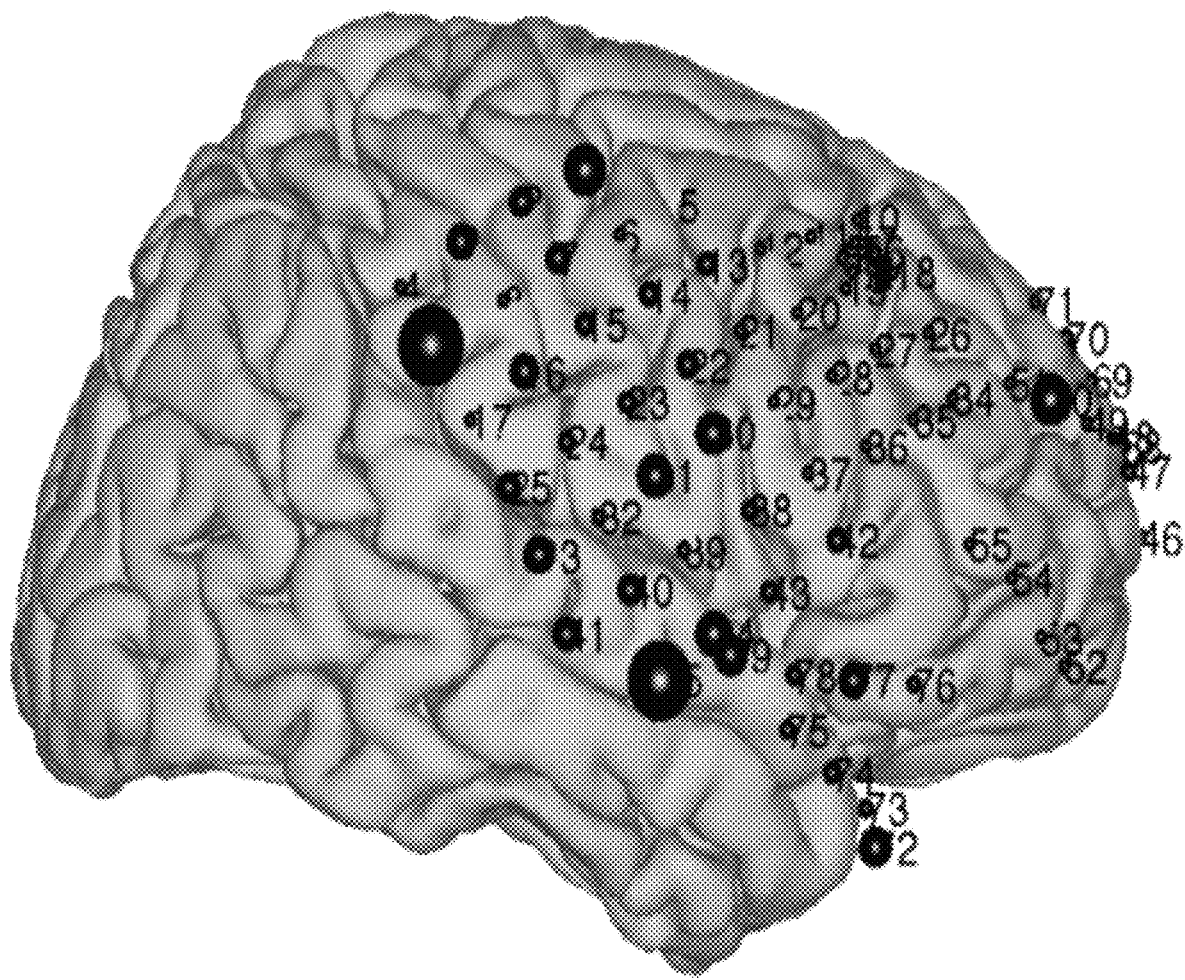
FIG. 2B is a topographical mapping showing placement of recording electrodes in a subject whose neural activity while the subject was awake was recorded.
Figure 2C:
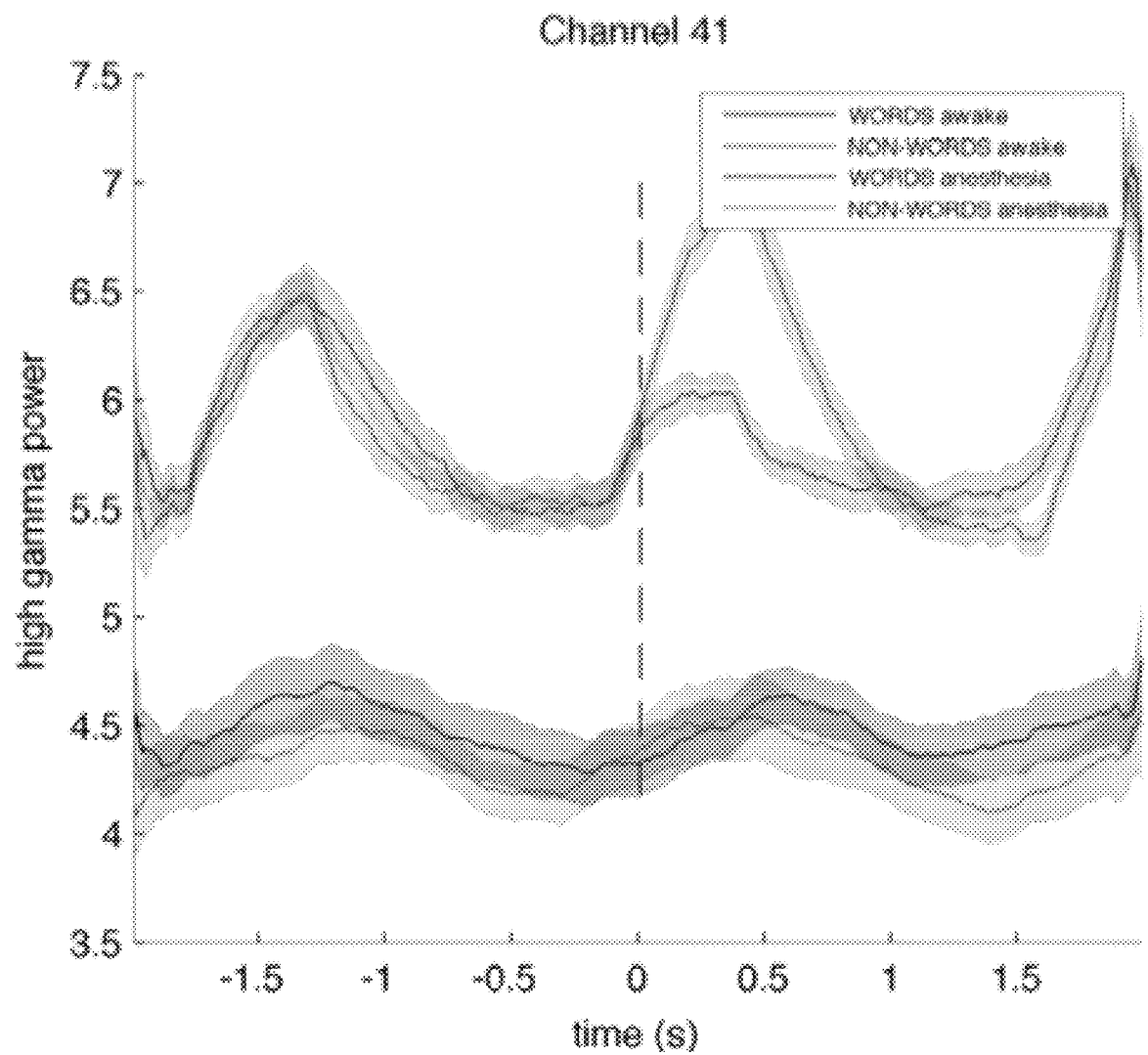
FIG. 2C, FIG. 2D, FIG. 2E, and FIG. 2F are graphs illustrating the results for receptive language mapping from various electrodes in a patient while awake and under anesthesia.
Figure 2D:
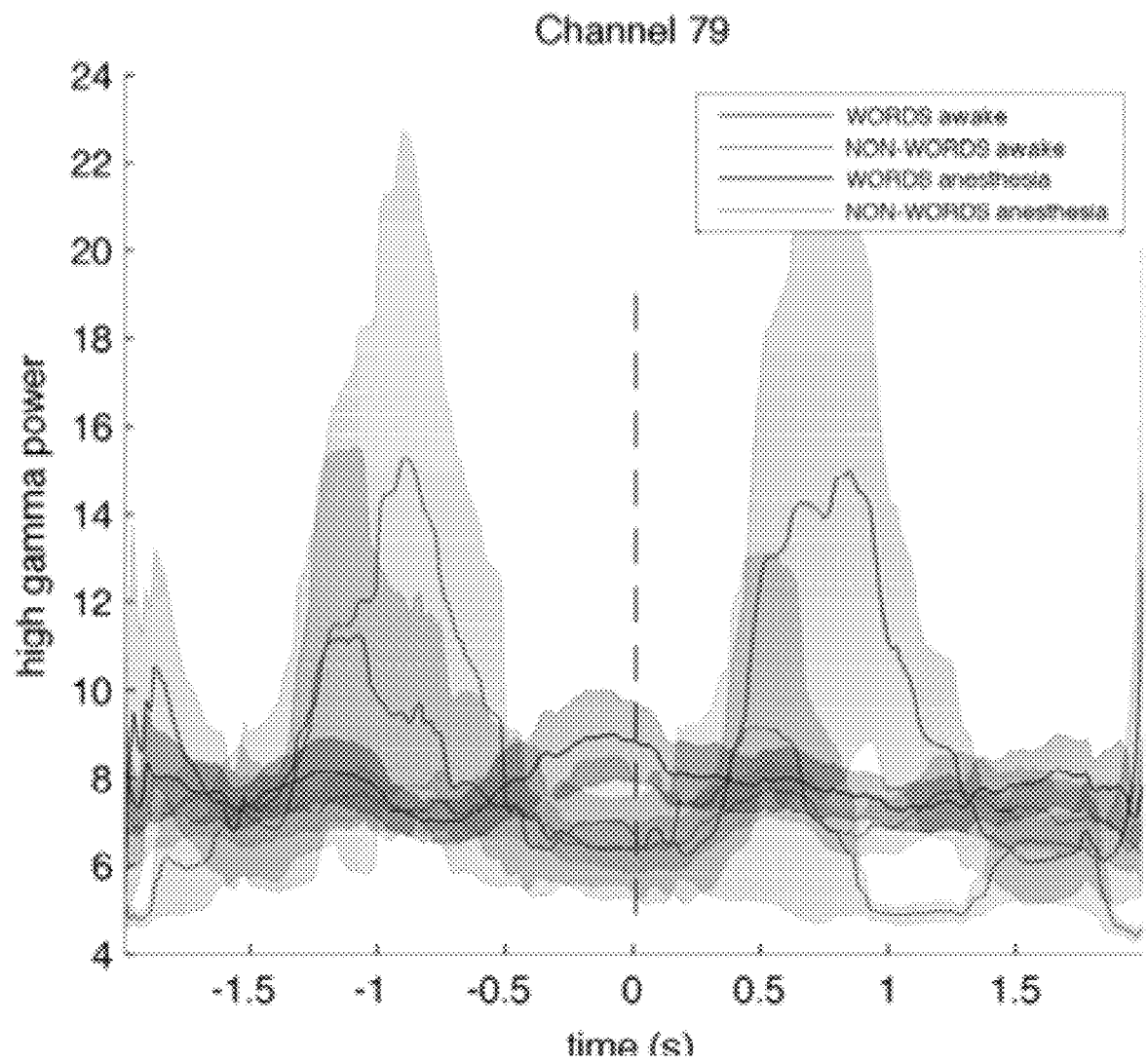
Figure 2E:
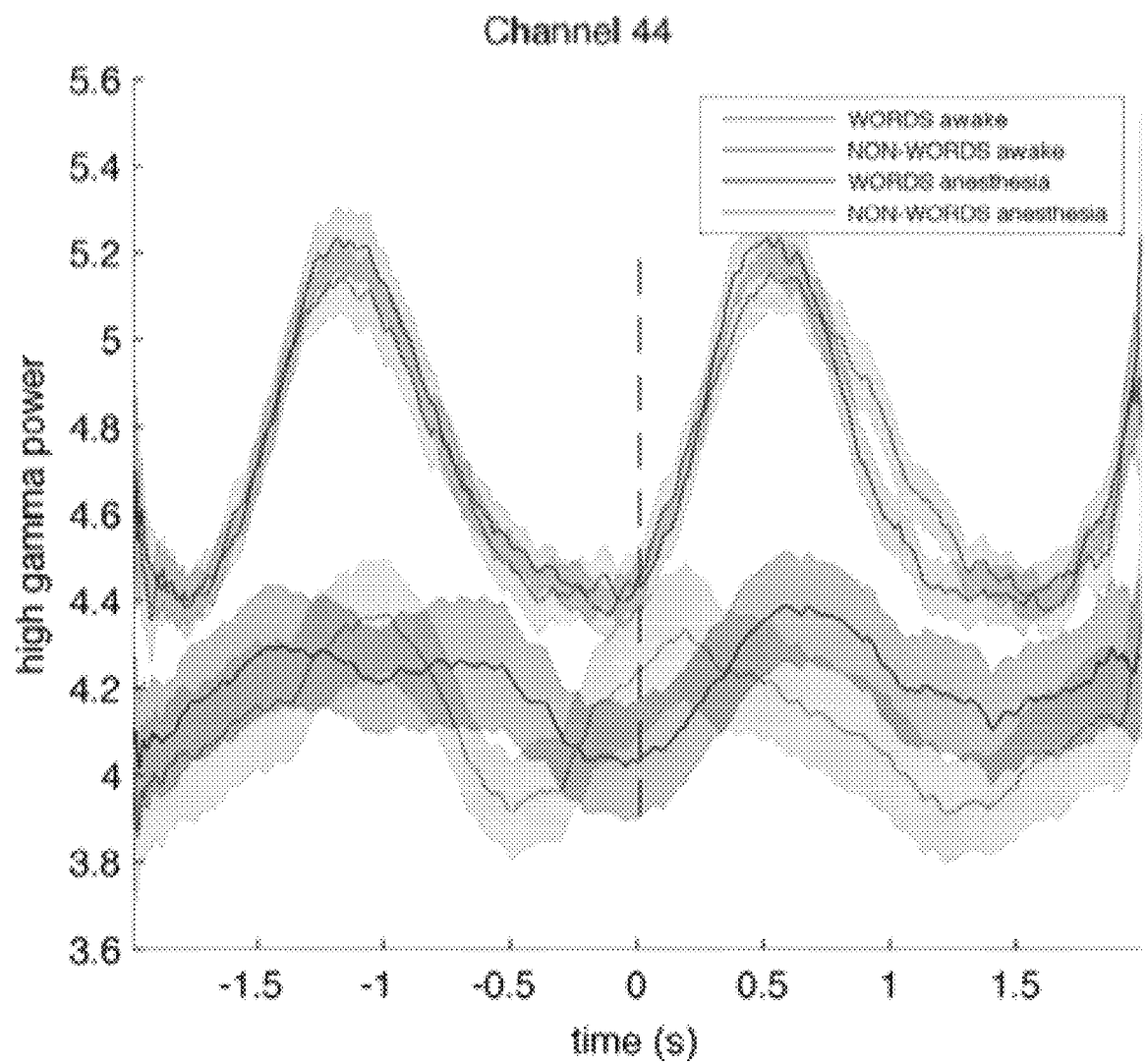
Figure 2F:
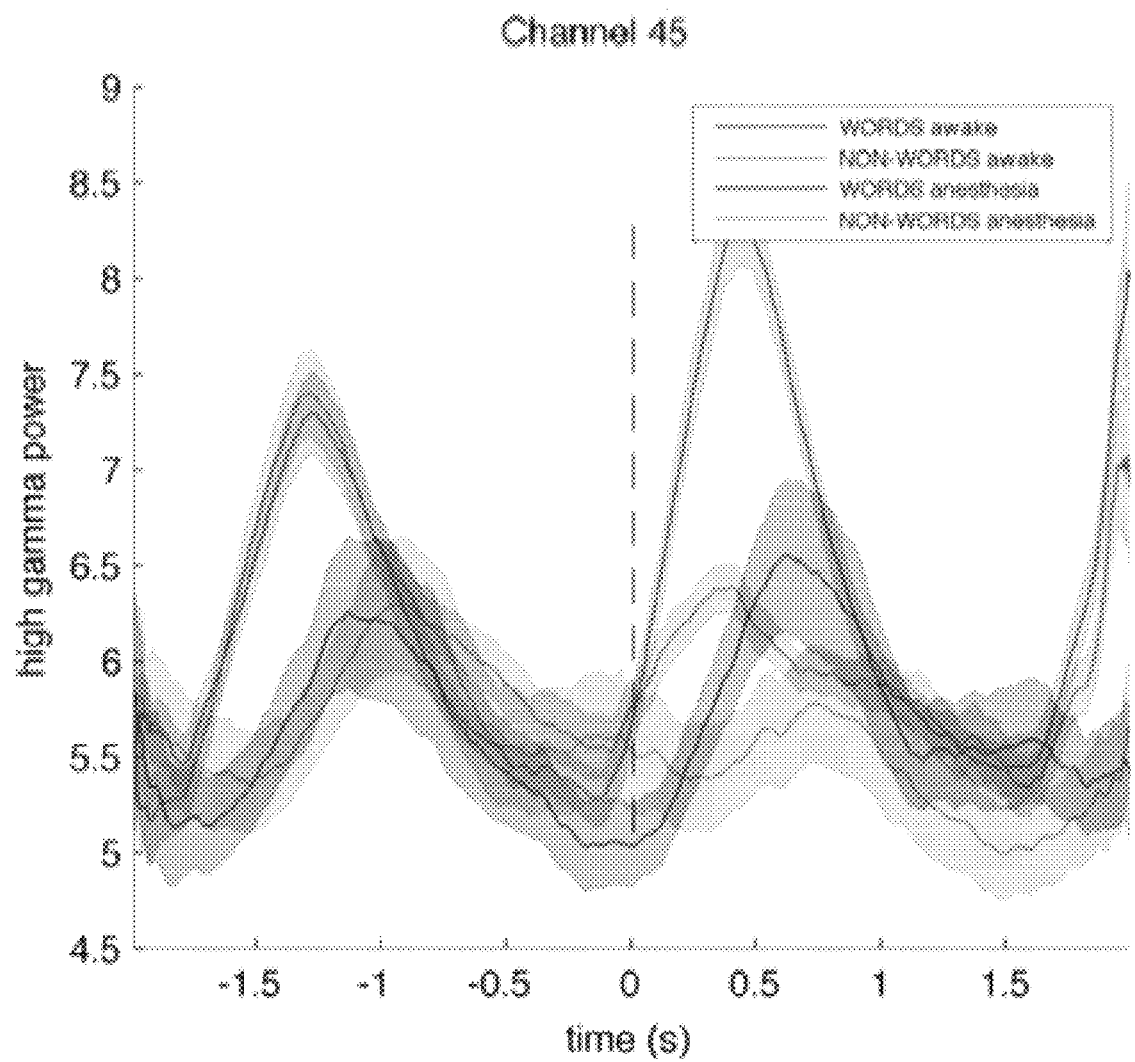

Mapping of Wernicke's area was validated under general anesthesia in one epileptic patient with right hemisphere coverage undergoing the second stage of a two-stage epilepsy surgery procedure. The electrode grid used for stimulation and recording covered the auditory and motor cortices but not Broca's area (confirmed by an absence of inferior frontal cortical responses during a verb generation task while the patient was awake). Two blocks were obtained while the patient was awake, and six while under propofol anesthesia. The recorded ECoG signals were band-pass filtered in the high gamma range (70-170 Hz) and averaged over trials. Electrode locations for mapping while awake are shown in FIG. 2A and while anesthetized in FIG. 2B. The results for four different locations (channels 41, 79, 44, and 45) are presented in FIGS. 2C-2F, respectively. Time courses for wave traces show the averaged high gamma responses to words (blue when the patient is awake, black under anesthesia) and non-words (red when the patent is awake, magenta under anesthesia). Time 0 indicates onset of stimulus. Location 44 is situated in the primary auditory cortex and responds equally to words and nonwords when the patient is awake (FIG. 2E). Location 45 is situated inferior to the primary auditory cortex, presumably in Wernicke's area. Its response to words is twice larger to its response to non-words (FIG. 2F). This dissociation between words and non-words is conserved during anesthesia despite a delay of the responses and the decrease by a factor 2 of their amplitude. (FIG. 2F).

Figure 3A:
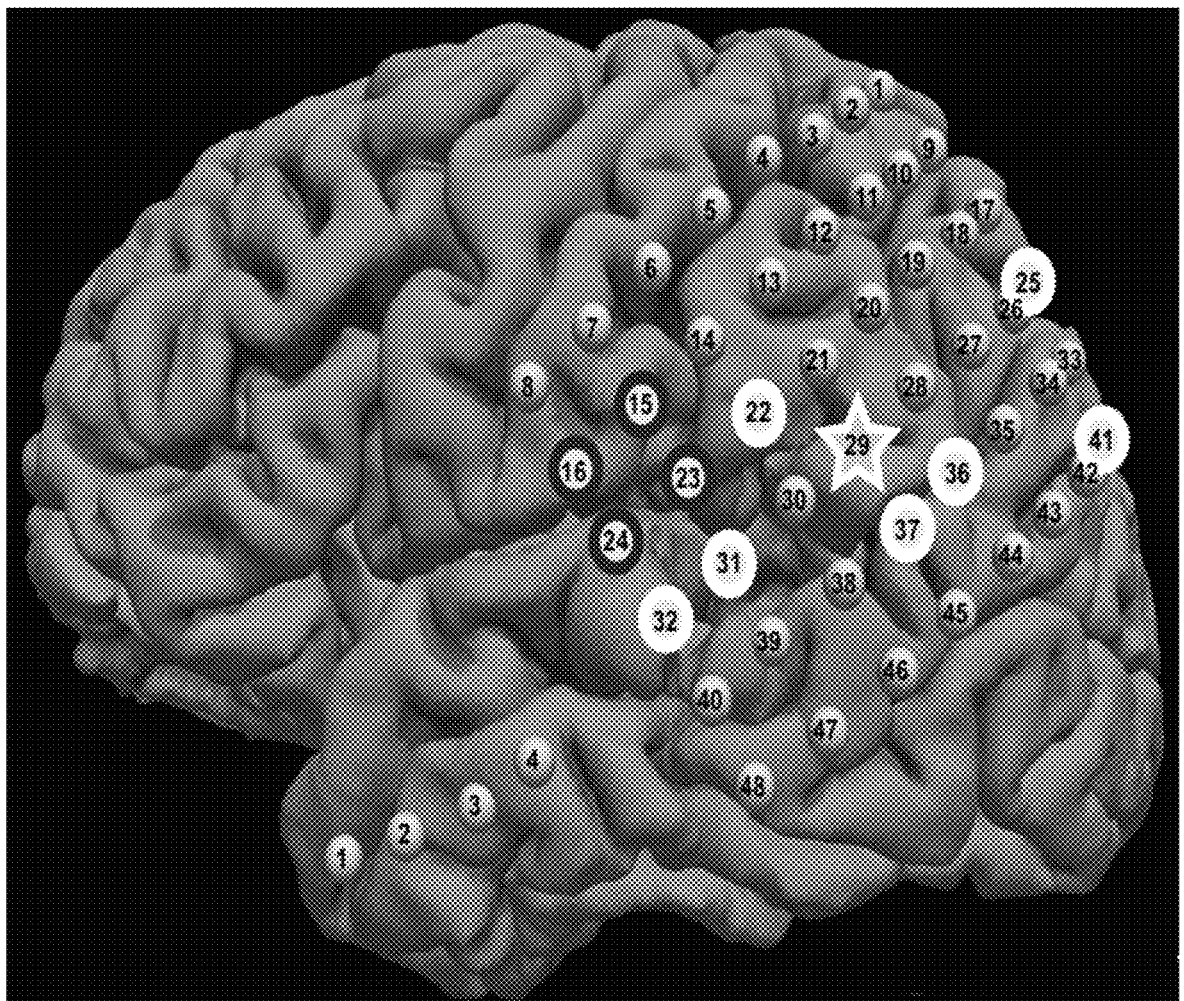
FIG. 3A is a topographical mapping showing placement of electrodes in a subject administered ECS for language mapping while awake and electrocorticography (ECoG) for language mapping while anesthetized.
Figure 3A:
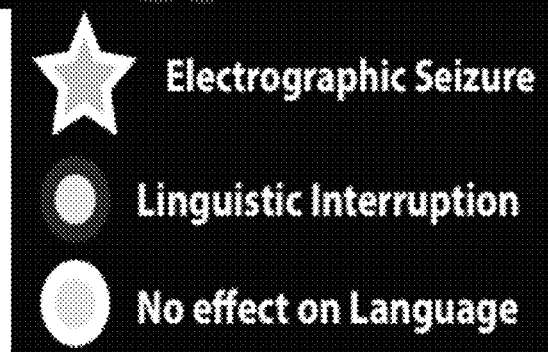
Figure 3B:
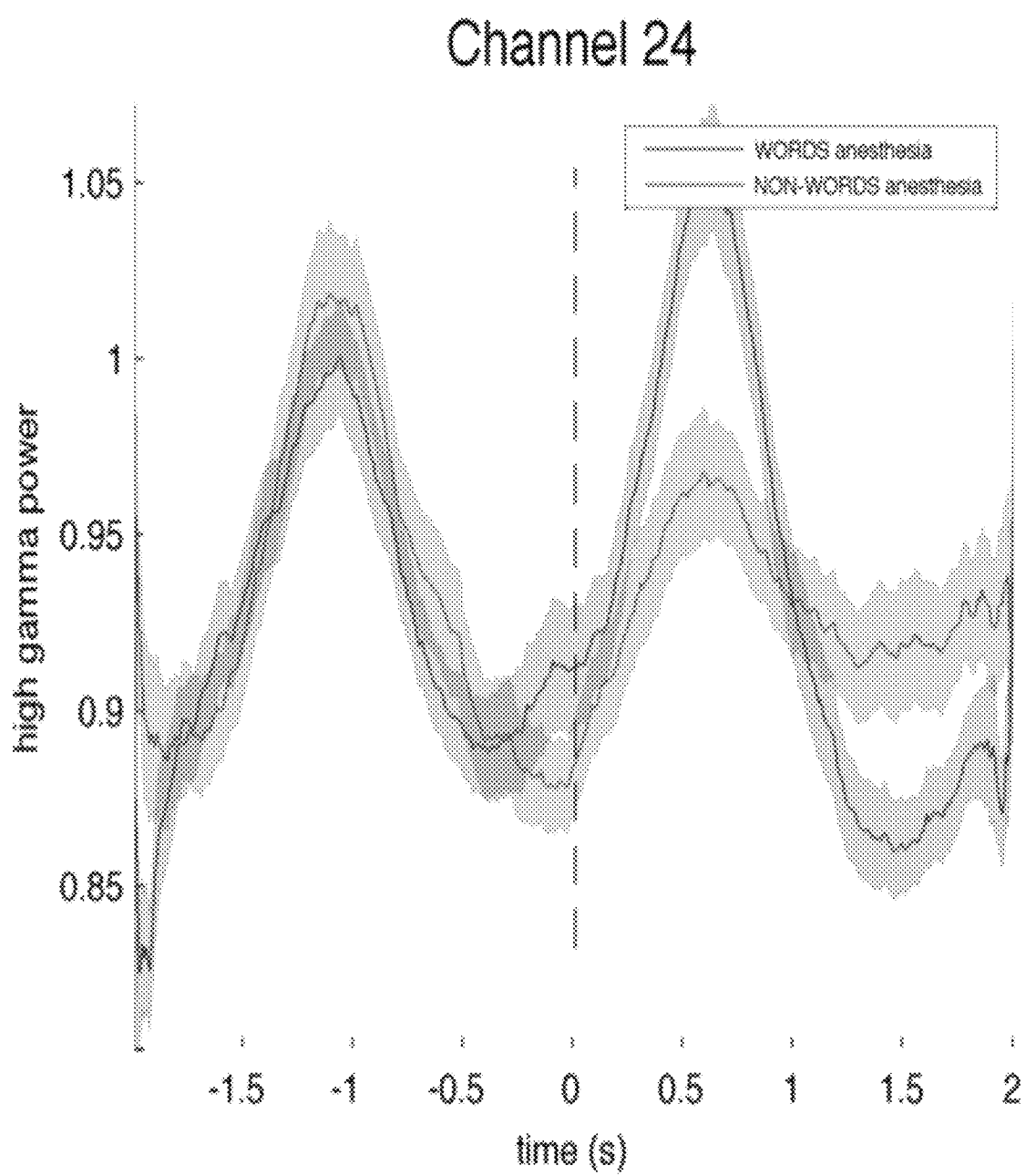
FIG. 3B is a graph illustrating the results of ECoG recording from an electrode demonstrating responsiveness to speech sounds in an anesthetized subject.

Results for another patient, following the foregoing protocol, are presented in FIG. 3A (electrode placement) and 3B (wave traces for averaged high gamma responses to words, in blue, and non-words, in red, when the patent is under anesthesia). ECoG signals at channel 24 (FIG. 3B) clearly respond to the auditory stimulus (words or non-words) that is presented at time 0, and responds differently for words (blue trace) and non-words (red trace).

Results from three additional subjects (A-C) were obtained in another example. All three subjects were patients at Albany Medical Center (Albany, N.Y.). Subject A was diagnosed with a low-grade glioma in the left frontal lobe after presenting with new-onset seizures. Subjects B and C suffered from intractable epilepsy. All subjects underwent temporary placement of subdural electrode grids to localize seizure foci and eloquent cortex prior to surgical resection. The electrode grids were approved for human use (Ad-Tech Medical Corp., Racine, Wis.; and PMT Corp., Chanhassen, Minn.) and covered different areas within frontal, temporal and parietal lobes of the left hemisphere. All three subjects had coverage of frontal lobe language areas and two of the three (subjects B and C) also had coverage of temporal lobe language areas. Electrodes consisted of platinum-iridium discs (4 mm in diameter, 2.3-3 mm exposed), were embedded in silicone, and were spaced 6-10 mm apart. The total number of implanted electrodes was 61, 98 and 134 in subjects A-C, respectively. Following subdural grid implantation, each subject had postoperative anterior-posterior and lateral radiographs, as well as computer tomography (CT) scans to verify grid location. Preoperative language lateralization (LL) had been assessed previously with fMRI in subject A and with WADA testing in subjects B and C. Based on these evaluations, language was lateralized to the left hemisphere in all three subjects.

Once subjects recovered postoperatively, ECoG signals were recorded at the bedside using general-purpose BCI2000 software, which controlled eight 16-channel g.USBamp biosignal acquisition devices (g.tec, Graz, Austria). To ensure integrity of clinical data collection, a connector split the electrode cables into two separate sets. One set was connected to the clinical monitoring system and another set was connected to the g.USBamp acquisition devices. ECoG signals were amplified, digitized at 1200 Hz and stored by BCI2000. Electrode contacts distant from epileptogenic foci and areas of interest were used for reference and ground.

3D cortical brain models were created for each subject by submitting preoperative high-resolution magnetic resonance imaging (MRI) scans to Freesurfer software (http://surfer.nmr.mgh.harvard.edu/). MRI scans were co-registered with post-operative CT images using SPM software (http://www.fil.ion.ucl.ac.uk/spm/), and the stereotactic coordinates of each grid electrode were identified using custom MATLAB scripts (The MathWorks Inc., Natick, Mass.). Finally, the cortical surface of each subject and ECoG grid locations were visualized using NeuralAct software.

Subjects were asked to listen to four short stories narrated by a male voice (stimulus duration: 17.15-35.70 s; inter-stimulus interval (ISI) of 10 s) that were part of the Boston Aphasia Battery. The stimuli were digitized at 44.1 kHz in waveform audio file format and binaurally presented to each subject using in-ear monitoring earphones (12 to 23.5 kHz audio bandwidth, 20 dB isolation from environmental noise). The sound volume was adjusted to a comfortable level for each subject. The subjects did not perform any overt task (such as repeating words, generating verbs in response to the words they heard, etc.).

ECoG activations were identified by detecting task-related changes in the broadband gamma (70-170 Hz) band. Activity in this band has been shown to be related to the average firing rate of neuronal populations directly underneath an electrode. A large number of studies have shown that broadband gamma activity increases reliably in task-related cortical areas, including locations traditionally thought to be active during speech perception.

To identify those locations that responded to auditory stimulation, channels that did not contain clear ECoG signals were first removed (e.g., ground/reference channels, channels with broken connections, or channels corrupted by environmental artifacts or interictal activity). Of a total of 61, 98 and 134 channels, this left 59, 79 and 132 channels for subjects A-C, respectively, that were submitted to subsequent analyses. In these analyses, the signals were highpass filtered at 0.1 Hz to remove drifts, and signals were rereferenced to a common average reference (CAR) montage. The results were band-pass filtered in the broadband gamma band using a Butterworth filter of order 16. The power of these signals was then obtained by computing the square of the analytical signal of the Hilbert transform, followed by a low-pass filter at 4 Hz and down-sampling to 120 Hz. Finally, the resulting broadband gamma power estimates were normalized by subtracting from them the signal mean calculated from a baseline period (−6 to −0.5 s prior to the onset of the auditory stimulus) and by dividing them by the standard deviation of the signal during the baseline period.

Those locations whose ECoG broadband gamma activity following onset of the auditory stimulus (i.e., the response period) was different from that during the baseline period were then determined. Several studies have shown that in receptive auditory areas, broadband gamma activity reliably tracks the time course of the envelope of the intensity of the auditory stimulus or speech stimulus. A few isolated reports documented discrete and brief broadband gamma activations in inferior frontal cortex after the onset of an auditory speech stimulus that occurred after the activations in receptive auditory areas. Based on these reports, the response period was defined as 250-750 ms following the onset of the auditory stimulus. Then, for each location, the magnitude of the change in ECoG broadband gamma power that was related to auditory stimulation by calculating the coefficient of determination (Pearson's r2 value) was determined. Finally, the statistical significance of each r2 value, i.e., the probability that ECoG broadband gamma samples differed in amplitude between the response and baseline periods, using a permutation test was determined. In this test, the ECoG broadband gamma power time courses were cut into blocks of 500 ms (thereby preserving the autocorrelation of the signal), the resulting blocks were randomly permutated, and finally the corresponding random r2 value was calculated. The permutation step was repeated 1000 times, thus generating a distribution of 1000 random r2 values at each location. r2 values were considered to be significant at the 95th percentile of that distribution (p=0.05, Bonferroni-corrected for the total number of electrodes in each subject). The result of this procedure was a set of locations whose ECoG broadband gamma activity was significantly different between the baseline and the response periods, and hence responded to the speech stimuli. Amongst the resulting locations, those that were situated within inferior frontal cortex were identified. This included all electrodes whose Talairach coordinate was within x −28 to −55, y −8 to +34, and z 0 to 28, consistent with previous observations.

Standard electrocortical stimulation mapping of expressive speech was performed extra-operatively for clinical purposes. The subjects took part in two simple tasks commonly used for this purpose: a picture naming task, during which subjects were asked to verbally name sequentially presented pictures of simple objects, and a verb generation task, during which subjects had to verbally generate verbs associated with simple nouns presented auditorily. Different electrode pairs were stimulated to establish whether a given pair induced disruption of expressive language function, e.g., speech arrest or hesitation. Stimulation intensity typically started at 2 mA and was increased in incremental steps of 2 mA until the neurologist observed clinical effects, after-discharges, or reached the 10 mA threshold.

Figure 4A:
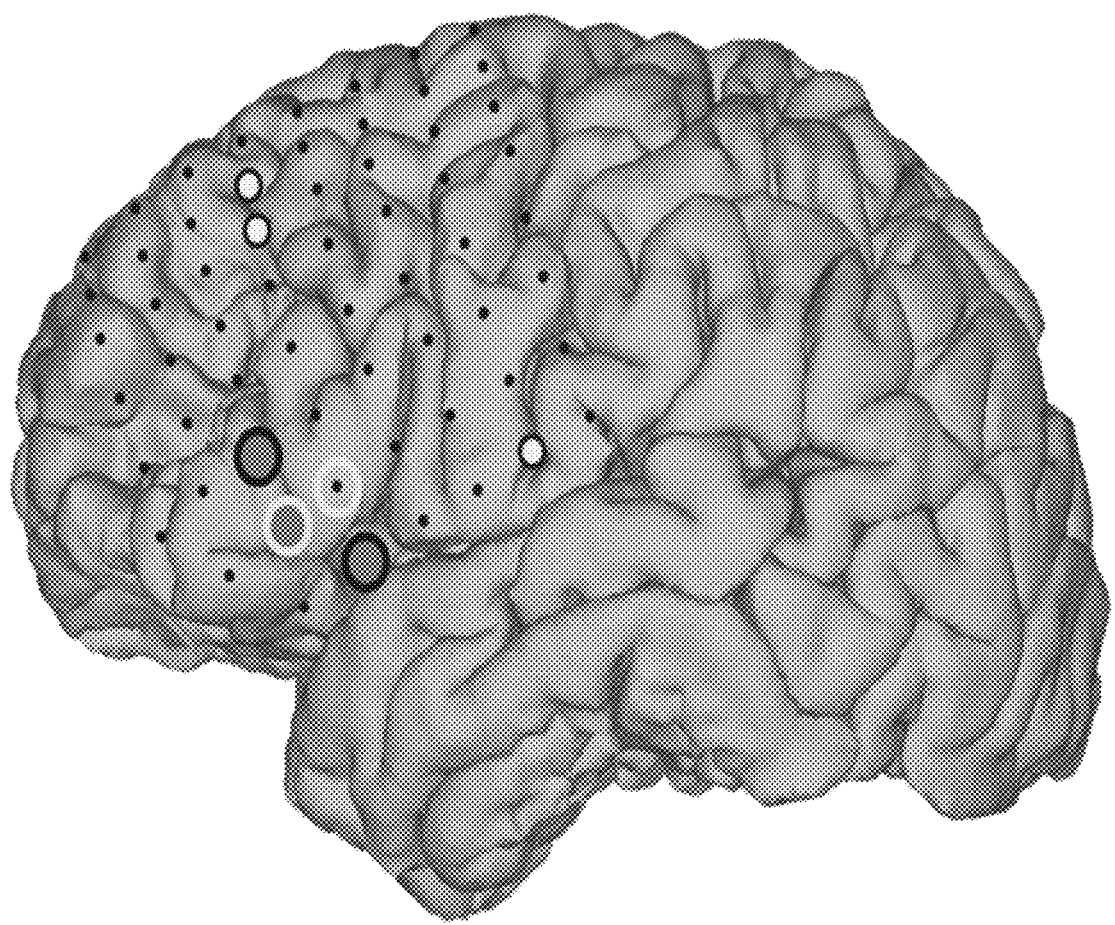
FIG. 4A, FIG. 4B, and FIG. 4C are diagrams and charts illustrating ECS and ECoG electrode placement and language area mapping results from three different patients.
Figure 4B:
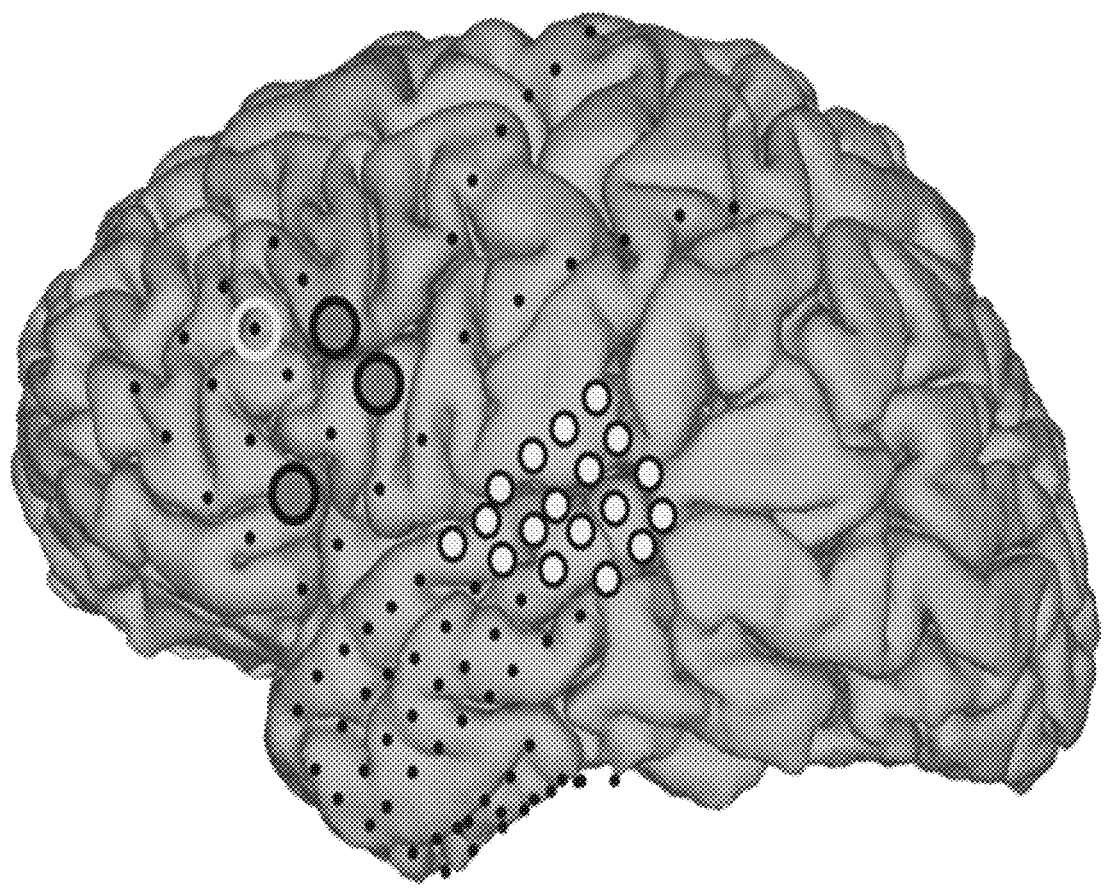
Figure 4C:
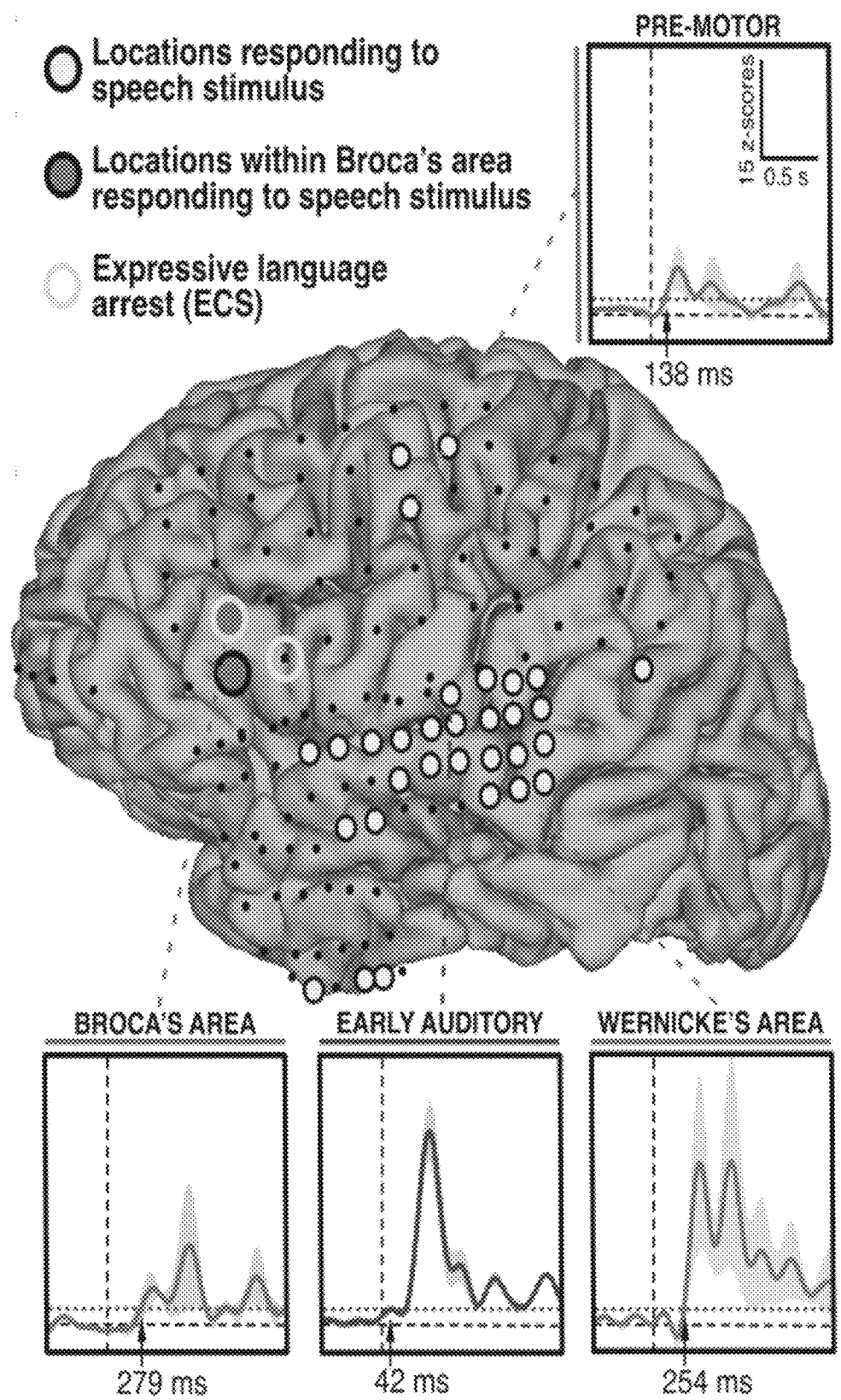

Results for subjects A, B, and C are presented in FIGS. 4A, 4B, and 4C, respectively. FIGS. 4A-4C highlight those locations that were identified by analyses of the ECoG signals corresponding to the presentation of the speech stimuli (filled circles), and locations that produced arrest of expressive language function using ECS mapping (yellow circles). Locations identified by ECoG mapping included the expected locations (highlighted by gray-filled circles) in superior temporal gyms and/or peri-sylvian areas (all subjects) as well as in premotor and/or supplementary motor areas (FIGS. 4A and 4C). Consistent with previous observations, responsive locations on or close to superior precentral gyms were also identified (FIG. 4C). Surprisingly, ECoG-based mapping identified expressive language locations (highlighted by blue-filled circles) in inferior frontal cortex (pars triangularis and/or pars opercularis) in subjects A, B, and C, (FIGS. 4A-4C, respectively). FIG. 4C also presents exemplary time courses of ECoG broadband gamma activity in Patient C.

ECS mapping identified 1-2 locations in which stimulation produced expressive language arrest in each subject (FIGS. 4A-4C, yellow circles). These locations were also located in or around pars triangularis and pars opercularis. ECS-positive sites overlapped with the sites identified using ECoG or were located no more than one contact away.

Figure 5:
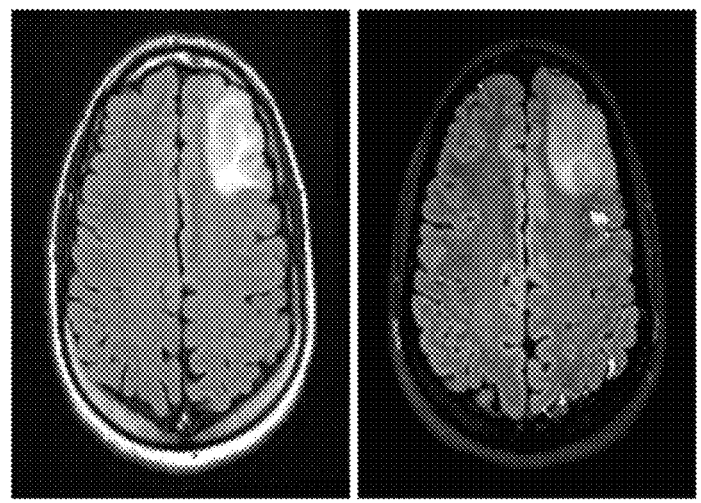
FIG. 5 shows a magnetic resonance (MR) image demonstrating the presence of a tumor in a subject (left) and functional magnetic resonance imaging (fMRI) showing the proximity of Broca's area to the tumor (right).

In another example, recordings were made of a 33 year-old male who presented after a motor vehicle accident while experiencing a first time seizure. The patient had a computerized tomography (CT) scan as part of his initial evaluation that suggested a hypodensity in the left frontal lobe. Magnetic resonance (MR) imaging revealed a nonenhancing left frontal mass (FIG. 5, left) and MR spectroscopy characteristics supported a low-to-medium grade tumor. Given the anatomic location of the tumor's proximity to presumed Broca's area, the patient underwent fMRI and diffusion tensor imaging (DTI). The fMRI confirmed the close relationship of the tumor to Broca's area (within 3-5 mm) with verb generation and object naming tasks (p<0.05, family-wise error correction) (FIG. 5).

The patient did not have any further seizures after the initiation of Keppra and he remained neurologically intact without any focal deficits or aphasia. To comprehensively evaluate expressive language cortex for an optimal postoperative outcome, the patient elected to pursue a two-staged brain mapping procedure with the use of subdural grids and ECS. Prior to surgery, the patient had neuropsychological testing for baseline evaluation using the Wechsler Adult Intelligence Scale WAIS-IV. The patient gave informed consent through a protocol that was reviewed and approved by the institutional review board of Albany Medical College as well as the US Army Medical and Materiel Command.

Figure 6A:
FIG. 6A and FIG. 6B show an 8×8 cm grid of 64 electrodes and its subdural placement on a subject's cortex, respectively.
Figure 6B:
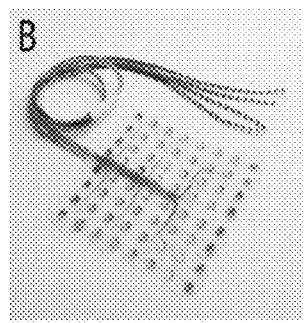
Figure 7A:
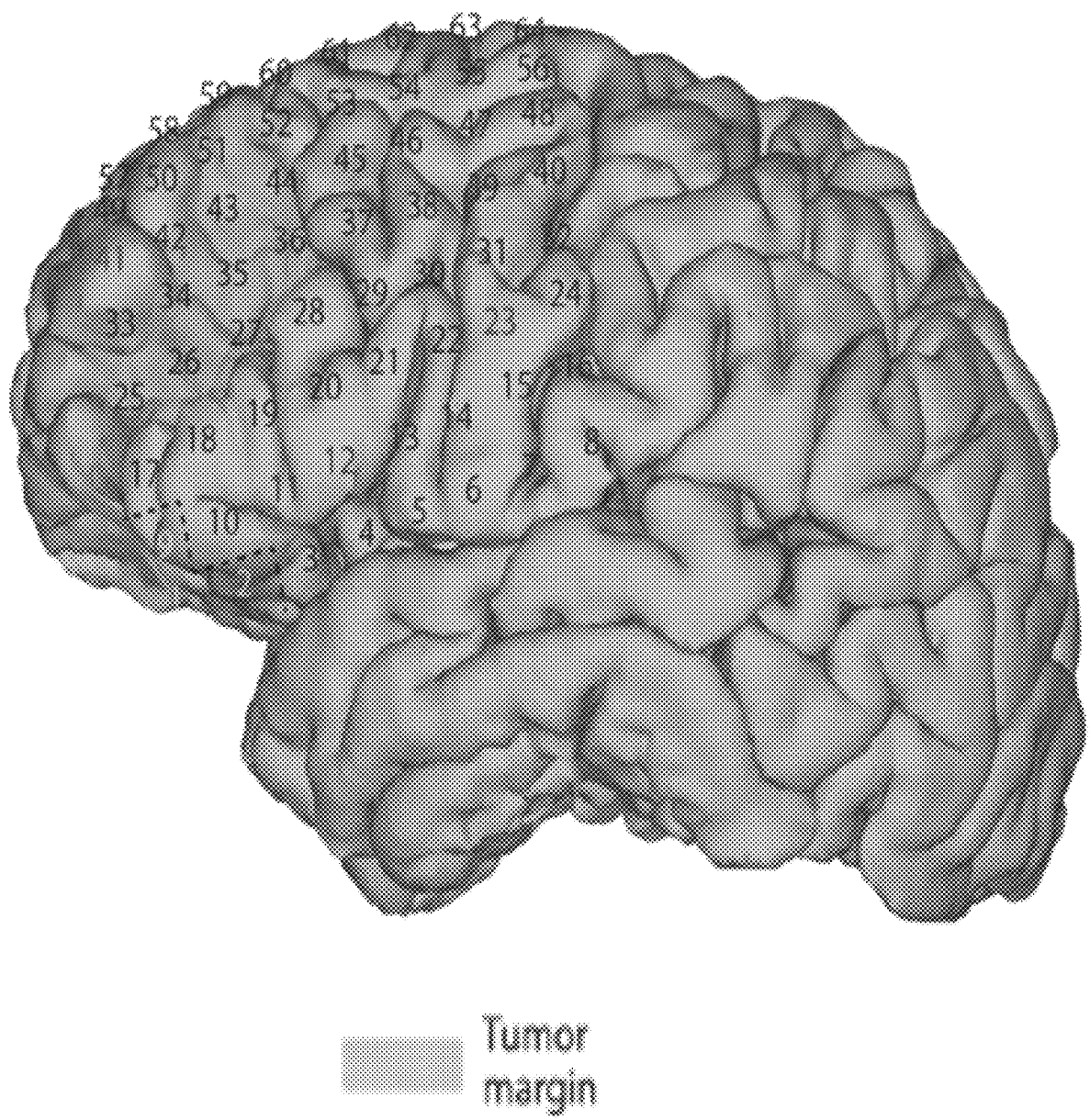
FIG. 7A shows electrode contacts of the standard subdural grid coverage in a subject with a tumor, whose location is indicated by blue shading.
Figure 7B:
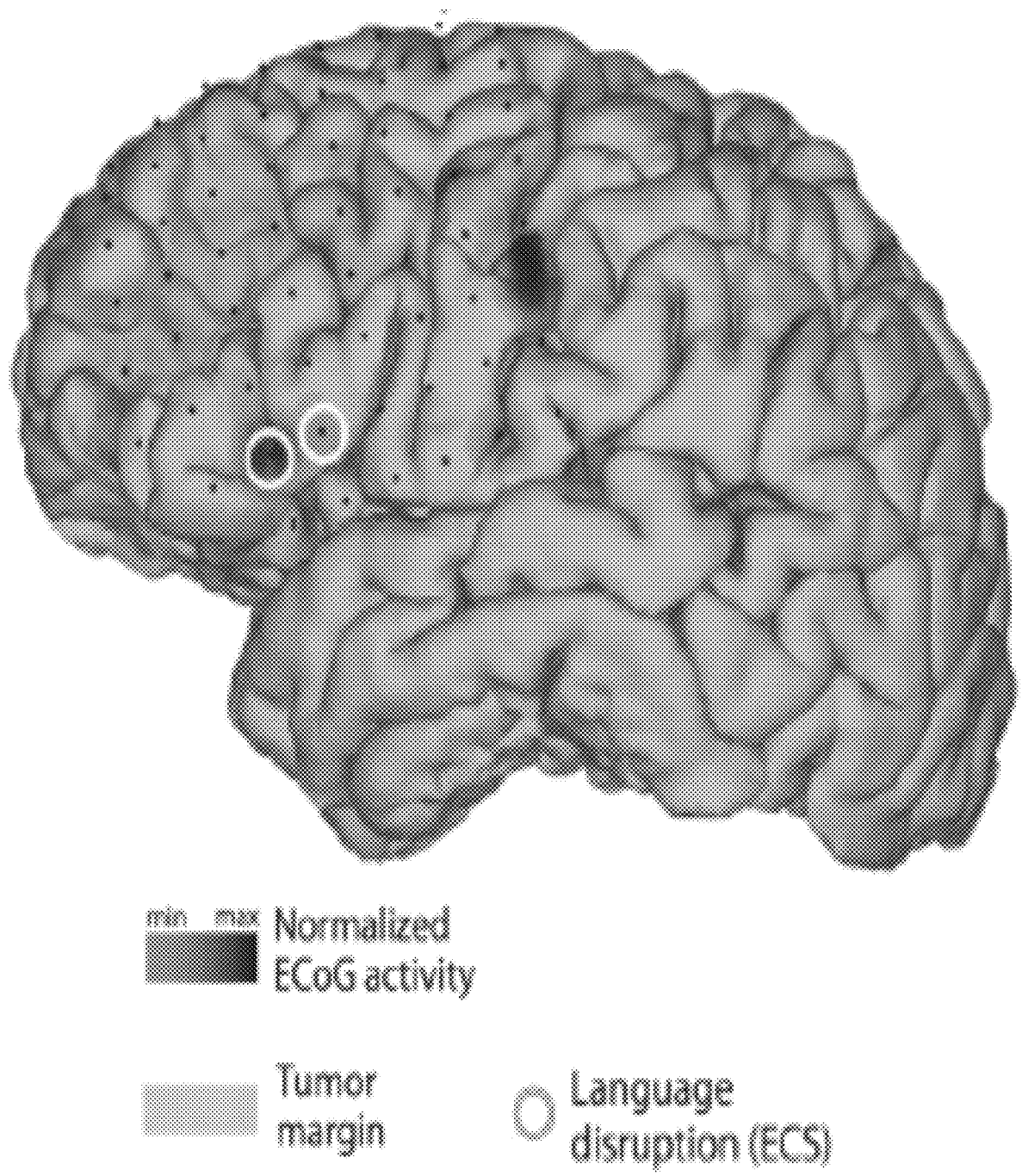
FIG. 7B Functional MRI showing increased BOLD activity (shown in yellow and orange) in Broca's area, as well as auditory/Wernicke's area, precentral gyms, supplementary motor/premotor cortex and prefrontal cortex.

For a first stage operation, the patient underwent implantation of an 8×8 cm silicon subdural grid embedded with 64 platinum iridium electrodes of 4 mm diameter (2.3 mm exposed) and inter-electrode distance of 1 cm [PMT, Chanhassen, Minn.] (FIGS. 6A and 6B). Contacts 1, 2 and 9 were removed for better contour along the cortical surface. Contact 57 was located most anteriorly, 64 most superiorly and contact 8 most posteriorly (FIG. 7A). A four-contact electrode strip was placed on the skull to provide a ground for the clinical monitoring system. The patient tolerated the first stage well and was connected to a Nihon-Kohden Neurofax video EEG monitoring system [Tokyo, Japan] that continuously recorded ECoG signals as well as accompanying clinical behavior. To ensure integrity of clinical data collection, passive splitter connectors simultaneously provided ECoG signals to eight optically isolated and synchronized 16-channel g.USBamp amplifier/digitizer units (g.tec, Graz, Austria) with signal sampling at 1200 Hz. Clinical review of ECoG signals identified frequent left frontal spikes and spike and wave discharges at contact 23.

On postoperative day 2, the patient underwent extraoperative functional cortical mapping in the epilepsy monitoring unit (EMU) with ECoG and ECS procedures. For ECoG mapping, the broadband gamma signal at each contact location was measured and compared between rest and task epochs to establish the statistical difference across these tasks. See Brunner et al. (2009) Epilepsy & Behavior, 15: 278-286. The patient first rested quietly for six minutes to establish a model of baseline ECoG activity. The patient then performed several repetitive motor and language tasks as instructed by visual cues: 1) solve Rubik's cube; 2) shrug shoulders; 3) stick out tongue; 4) purse lips; 5) listen to a narrative; 6) generate verbs; and 7) imagine generating verbs. This ECoG paradigm identified electrode contacts 11 and 12 (FIG. 7A) as expressive language nodes within a few minutes.

For the ECS procedure, a digital Grass S12X stimulator with built-in stimulus isolation and constant current circuitry [Grass Technologies, Warwick, R.I.] was used to stimulate pairs of electrodes using a pulse duration of 0.3 ms, variable frequencies between 20-50 Hz, current ranging from 1-15 mA and train durations of 5 s. Bipolar and monopolar modalities were assessed with increasing current until afterdischarges or a functional response was elicited, or the maximum amount of current was reached at 15 mA. Stimulation of contacts 11 and 12 with 10 mA at 20 Hz rendered complete speech arrest, indicating eloquence. These nodes were confirmed on four separate occasions throughout the procedure. Oral motor function was also identified. An electrographic seizure was elicited with stimulation of contacts 23 and 41 during mapping; the patient was treated with 2 mg IV Ativan, 1000 mg IV Keppra and 500 mg Fosphenytoin. Further mapping was delayed for approximately 90 minutes due to the stimulus-induced seizure and subsequent postictal period.

Figure 6C:
FIG. 6C and FIG. 6D show a 2.5×2.5 cm grid of 64 electrodes and its subdural placement on a subject's cortex, respectively.
Figure 6D:
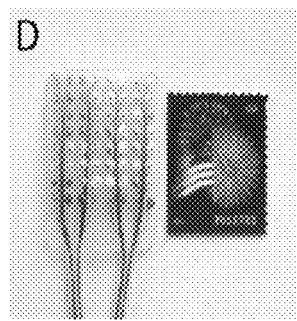

For a second stage operation, five days after the initial subdural grid implantation, the patient returned to the operating room for the second stage. Once the previous craniotomy flap was reopened and the cortical surface was exposed with good hemostasis, the standard subdural grid was replaced with a high-density 64-contact silicon grid (PMT Corp., Chanhassen, Minn.), measuring 2.5×2.5 cm embedded with platinum iridium electrodes of 2 mm diameter (1 mm exposed) and with an interelectrode distance of 3 mm (FIGS. 6C and 6D). To further refine the boundary of expressive language function, this high-density grid covered only the language cortex previously identified by extraoperative ECoG and ECS mapping. The patient was reversed from anesthesia for awake passive mapping. Within minutes, intraoperative ECoG mapping using verb generation and word repetition identified the most significant ECoG changes at locations corresponding to contacts 11 and 12 of the original standard subdural grid. These locations were outlined for preservation. The patient tolerated the procedure very well and was induced back under anesthesia for the remainder of the surgery.

Postoperatively, the patient experienced an excellent recovery and had very mild issues of transient confusion. Permanent pathology revealed focal anaplasia WHO III in the setting of diffuse fibrillary astrocytoma WHO II.

Mapping results from fMRI, ECS, and extra- and intraoperative ECoG are summarized in FIGS. 7A-7D. For fMRI data acquisition, preoperative scans were acquired on a Philips Ingenia 3T scanner with an echo planar imaging (EPI) sequence (80 scans, acquisition voxel size 3 mm isotropic, repetition time (TR) 3 s, echo time (TE) 30 ms, flip angle 90 degrees, field of view (FOV) 237 mm). Functional MRI data were preprocessed and analyzed using statistical parametric mapping software (SPM8, http://www.fil.ion.ucl.ac.uk/spm). Images were re-aligned and co-registered with an anatomical scan using normalized mutual information. Statistical analyses were performed on a single-subject basis and therefore no smoothing was applied. A general linear model was estimated with one regressor for verb generation (a 15 s box car for verb generation blocks convolved with a standard hemodynamic response function), data were corrected for low frequency drifts by a 128 s high pass filter and corrected for serial correlations with a first-order autoregressive model. Functional MRI results were rendered on the surface of the cortex (FIG. 7B) in similar manner as published previously, plotting any activation up to 8 mm below the surface. Functional MRI activity was plotted with a threshold of $t(150)>5.51$, pFWEcorrected<0.05.

A three-dimensional patient-specific cortical surface brain model was created by submitting the preoperative high resolution MRI scans to Freesurfer (http://surfer.nmr.mgh.harvard.edu). The stereotactic coordinates of the standard subdural grid were identified using SPM8 software (http://www.fil.ion.ucl.ac.uk/spm/) and custom MATLAB scripts (The MathWorks Inc., Natick, Mass.), which co-registered the MRI scans with the postoperative CT scans. The high-density subdural grid contacts were co-registered with those of the standard subdural grid using scalp fiducial markers, an intraoperative neuronavigation system (BrainLab AG, Feldkirchen, Germany) and novel custom software. The electrode locations were then projected onto a three-dimensional brain model and custom NeuralAct software (FIG. 7C) to render activation maps of corresponding ECoG activity.

Figure 7C:
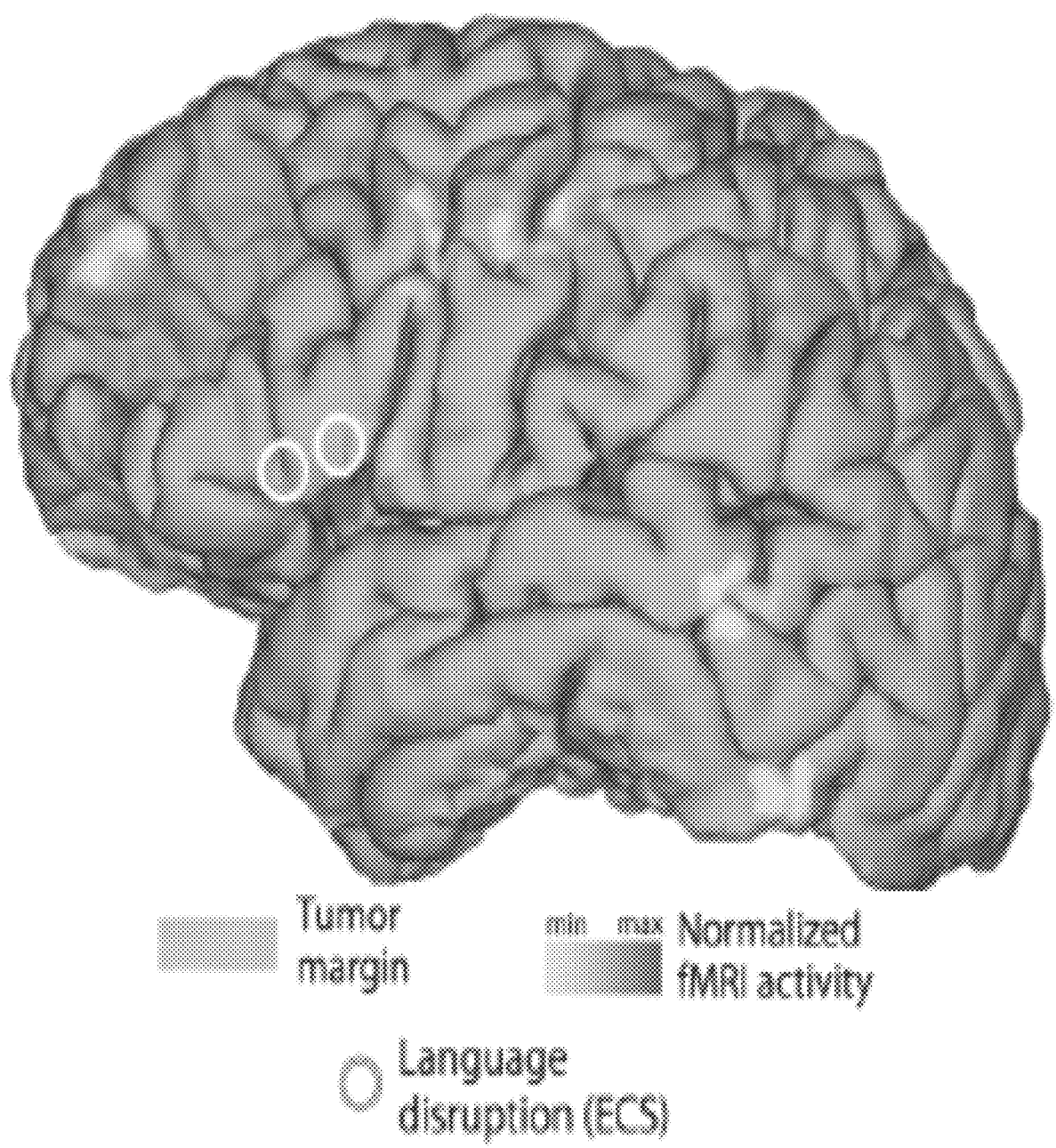
FIG. 7C Electrode contacts of a standard extraoperative subdural grid, and results from extraoperative ECoG-based functional language area mapping (shown in green) demonstrating increased activity in Boca's area, precentral gyms, supplementary motor/premotor cortex and postcentral gyms.
Figure 7D:
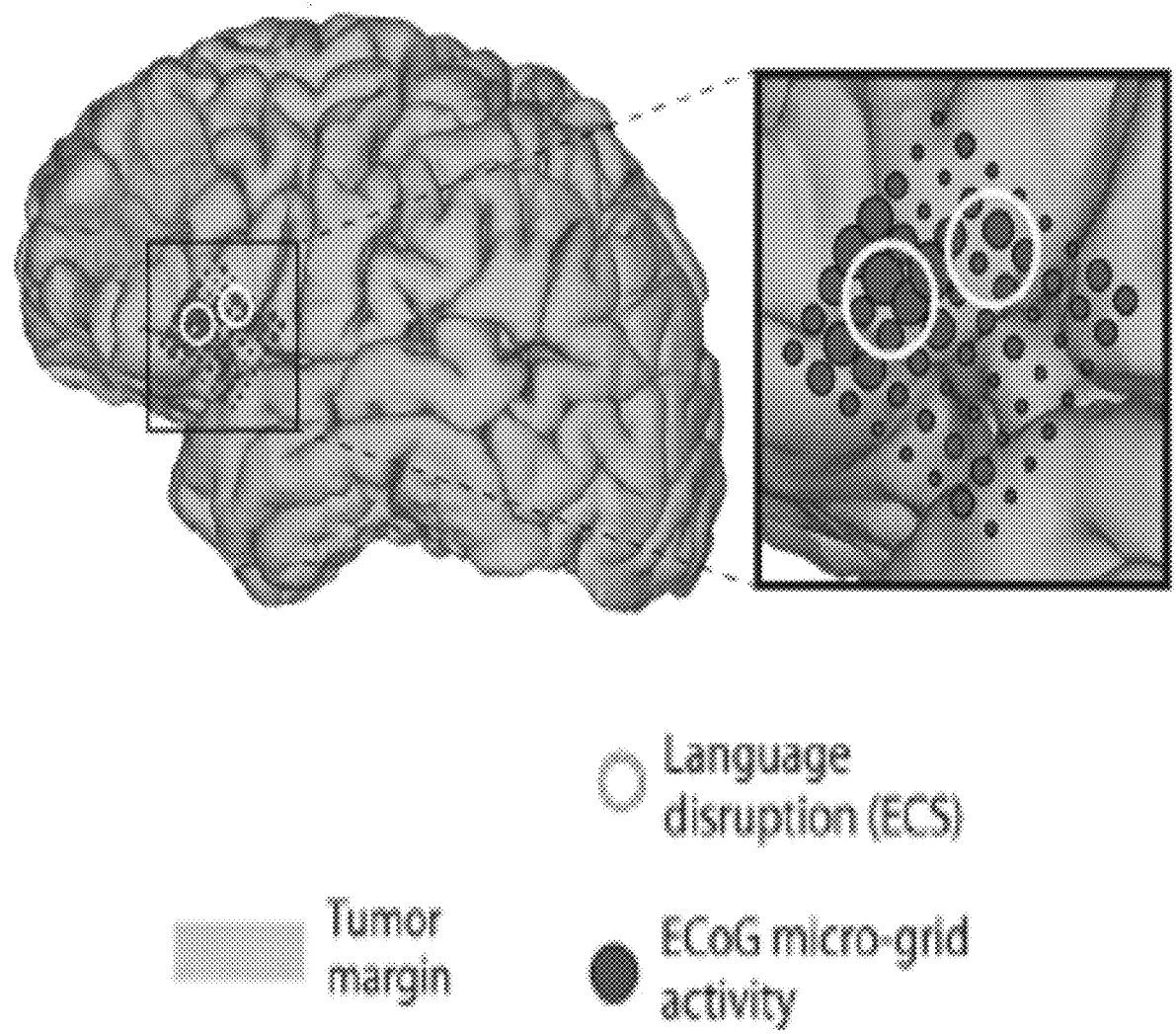
FIG. 7D shows results from intraoperative ECoG-based functional language mapping.

ECS and extraoperative ECoG delineated identical critical language nodes using a standardized grid coordinate system (FIG. 7C). The same locations were confirmed with intraoperative high-resolution ECoG (FIG. 7D). These results demonstrate the value of passive ECoG-based mapping in the extraoperative as well as the intraoperative environment.

Figure 8:
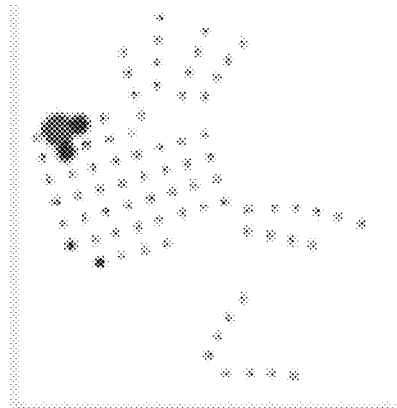
FIG. 8 is diagrams illustrating the result of ECoG-based brain mapping of brain areas responsible for sensory function of the index finger in a subject.
Figure 8:
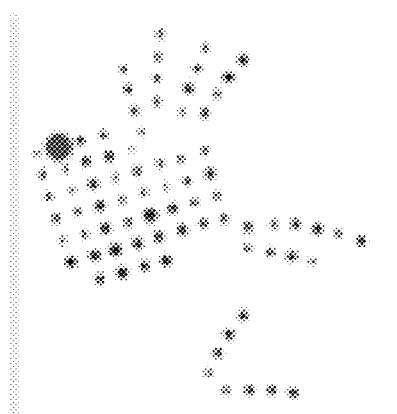

In another example, testing was conducted to map brain areas responsible for sensory function, according to recording methods as described above. FIG. 8 illustrates the result of ECoG-based brain mapping of brain areas responsible for sensory function of the index finger in a subject. As shown in FIG. 8, each dot represents one electrode. The diameter of each electrode is proportional to the change in ECoG amplitude in the gamma (i.e., >70 Hz) range between rest and sensory stimulation. The locations identified using this procedure are similar to when the patient was awake (FIG. 8, top) compared to when the patient was under anesthesia (FIG. 8, bottom). The magnitude of the effect (see color bars) is noticeably smaller during anesthesia. These results demonstrate the importance of using ECoG to map brain areas responsible for sensorimotor functions in anesthetized or unresponsive patients in a perioperative setting.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be understood that the terms "comprise", "have", "include", and "contain" (and any related variants thereof) are open-ended linking verbs. As a result, a method, step, or device that "comprises", "has", "includes" or "contains" one or more steps or elements possesses those one or more steps or elements, but is not limited to possessing only those one or more steps or elements. The corresponding structures, materials, acts, and equivalents of all means or step plus function elements in the claims below, if any, are intended to include any structure, material, or act for performing the function in combination with other claimed elements as specifically claimed. The disclosure herein is illustrative and not intended to be exhaustive or limited to the invention in the form disclosed. Many modifications and variations will be apparent to those of ordinary skill in the art without departing from the scope and spirit of the invention. Embodiments are described to best explain the principles of one or more aspects of the invention and the practical application, and to enable others of ordinary skill in the art to understand one or more aspects of the invention for various embodiments with various modifications as are suited to the particular use contemplated.

What is claimed is:

1. A method for mapping a neural area involved in speech processing comprising:
    applying a plurality of recording electrodes to a surface of a cortex of a human subject;
    presenting a plurality of auditory stimuli to the subject wherein some of the plurality of stimuli are speech sounds and others of the plurality of auditory stimuli are non-speech sounds;
    recording brain activity during the presenting of the plurality of auditory stimuli; and
    identifying one or more brain areas wherein the brain activity of the one or more brain areas changes more after presentation of the speech sounds than it does after presentation of the non-speech sounds;
    wherein the human subject is unconscious and does not speak during the presenting and the recording.

2. A method according to claim 1, wherein the human subject is anesthetized during the presenting and the recording.

3. A method according to claim 2, wherein one or more of the plurality of recording electrodes includes a diameter of an exposed surface of approximately 1 cm.

4. A method according to claim 2, wherein the brain activity of the one or more brain areas changes within between 250-750 ms after an onset of presentation of the plurality of auditory stimuli.

5. A method of claim 2, wherein identifying comprises converting an analog recording of the brain activity to a digital recording of the brain activity and identifying one or more brain areas wherein broadband gamma waves of the one or more brain areas changes more after presentation of the speech sounds than it does after presentation of the non-speech sounds.

6. A method according to claim 1, further comprising mapping a neural area involved in speech production and applying a plurality of recording electrodes to a surface of a frontal cortex of the human subject.

7. A method according to claim 1, further comprising mapping a neural area involved in speech reception and applying a plurality of recording electrodes to a surface of a temporal cortex of the human subject.

8. A method according to claim 1, wherein one or more of the plurality of recording electrodes includes a diameter of an exposed surface of less than approximately 2.5 mm.

9. A method according to claim 8, wherein one or more of the plurality of recording electrodes includes a diameter of an exposed surface of approximately 1 mm.

10. A method according to claim 1, comprising an inter-electrode distance of 1 cm or less.

11. A method according to claim 10, comprising an inter-electrode distance of 3 mm or less.

12. A method according to claim 1, wherein the brain activity of the one or more brain areas changes within between 100-1000 ms after an onset of presentation of the plurality of auditory stimuli.

13. A method according to claim 12, wherein the brain activity of the one or more brain areas changes within between 250-750 ms after an onset of presentation of the plurality of auditory stimuli.

14. A method according to claim 1, wherein the change in activity of the one or more brain areas occurs for a duration that is shorter than a duration during which the speech sounds are presented.

15. A method according to claim 14 wherein the change in activity of the one or more brain areas occurs for less than 1000 ms during presentation of the speech stimulus wherein the speech sounds are presented for more than 1000 ms.

16. A method according to claim 1 wherein the change in activity of the one or more brain areas occurs for substantially all of a duration during which the speech sounds are presented.

17. A method according to claim 1, wherein recording brain activity comprises recording broadband gamma waves.

18. The method of claim 17, wherein identifying comprises identifying one or more brain areas wherein broadband gamma waves of the one or more brain areas changes more after presentation of the speech sounds than it does after presentation of the non-speech sounds.

19. A method of claim 1, wherein recording brain activity comprises recording oscillatory activity and the oscillatory activity is one or more of theta, alpha, or beta activity.

20. A method of claim 1, wherein recording brain activity comprises recording evoked potential activity.

21. A method according to claim 1, wherein identifying comprises converting an analog record of brain activity to a digital record of brain activity.

22. The method of claim 21 further comprising using a hardware processor to control the time of onset of the plurality of auditory stimuli and to measure the change in brain activity of the one or more brain areas after presentation of the plurality of auditory stimuli.

23. The method of claim 22, wherein identifying comprises identifying one or more brain areas wherein broadband gamma waves of the one or more brain areas changes more after presentation of the speech sounds than it does after presentation of the non-speech sounds.

24. A method for mapping a neural area involved in speech processing comprising:
    applying a plurality of recording electrodes to a surface of a cortex of a human subject wherein one or more of the plurality of recording electrodes includes a diameter of an exposed surface of approximately 1 cm and an inter-electrode distance of 1 cm or less;
    presenting a plurality of auditory stimuli to the subject wherein some of the plurality of stimuli are speech sounds and other of the plurality of auditory stimuli are non-speech sounds;

recording broadband gamma waves during the presenting of the plurality of auditory stimuli, wherein the broadband gamma waves indicate brain activity; and converting an analog recording of the brain activity to a digital recording of the brain activity and identifying one or more brain areas wherein broadband gamma waves of the one or more brain areas changes more within between 100-1000 ms after an onset of presentation of the speech sounds than it does within between 100-1000 ms after an onset of presentation of the non-speech sounds; and using a hardware processor to control the time of onset of the plurality of auditory stimuli and to measure a change in the brain activity of the one or more brain areas after presentation of the plurality of auditory stimuli;

wherein the subject is unconscious and does not speak during the presenting and the recording.

25. A method according to claim 24, wherein one or more of the plurality of recording electrodes includes a diameter of an exposed surface of approximately 1 mm.

26. A method according to claim 24, comprising an inter-electrode distance of 3 mm or less.

27. A method according to claim 24, wherein the brain activity of the one or more brain areas changes within between 250-750 ms after an onset of presentation of the plurality of auditory stimuli.

28. A method for mapping a neural area involved in speech production comprising:

applying a plurality of recording electrodes to a surface of a cortex of a human subject;

presenting a plurality of auditory stimuli to the subject wherein some of the plurality of stimuli are speech sounds and others of the plurality of auditory stimuli are non-speech sounds;

recording brain activity during the presenting of the plurality of auditory stimuli; and identifying one or more brain areas wherein the brain activity of the one or more brain areas changes more after presentation of the speech sounds than it does after presentation of the non-speech sounds;

wherein the human subject is unconscious and does not speak during the presenting and the recording.

29. A method according to claim 28, wherein the human subject is anesthetized during the presenting and the recording.

30. A method according to claim 29, wherein one or more of the plurality of recording electrodes includes a diameter of an exposed surface of approximately 1 cm.

31. A method according to claim 29, wherein the brain activity of the one or more brain areas changes within between 250-750 ms after an onset of the presentation of a plurality of auditory stimuli.

32. A method of claim 29, wherein identifying comprises converting the analog recording of brain activity to a digital recording of brain activity and identifying one or more brain areas wherein broadband gamma waves of the one or more brain areas changes more after presentation of the speech sounds than it does after presentation of the non-speech sounds.

33. A method according to claim 28, wherein one or more of the plurality of recording electrodes includes a diameter of an exposed surface of less than approximately 2.5 mm.

34. A method according to claim 33, wherein one or more of the plurality of recording electrodes includes a diameter of an exposed surface of approximately 1 mm.

35. A method according to claim 28, comprising an inter-electrode distance of 1 cm or less.

36. A method according to claim 35, comprising an inter-electrode distance of 3 mm or less.

37. A method according to claim 28, wherein the brain activity of the one or more brain areas changes within between 100-1000 ms after an onset of presentation of the plurality of auditory stimuli.

38. A method according to claim 37, wherein the brain activity of the one or more brain areas changes within between 250-750 ms after an onset of presentation of the plurality of auditory stimuli.

39. A method according to claim 28, wherein the change in brain activity of the one or more brain areas occurs for a duration that is shorter than a duration during which the speech sounds are presented.

40. A method according to claim 39 wherein the change in brain activity of the one or more brain areas occurs for less than 1000 ms during presentation of the plurality of auditory stimulus wherein the speech stimulus is presented for more than 1000 ms.

41. A method according to claim 28, wherein recording brain activity comprises recording broadband gamma waves.

42. The method of claim 41, wherein identifying comprises identifying one or more brain areas wherein the broadband gamma waves of the one or more brain areas changes more after presentation of the speech sounds than it does after presentation of the non-speech sounds.

43. A method of claim 28, wherein recording brain activity comprises recording oscillatory activity and the oscillatory activity is one or more of theta, alpha, or beta activity.

44. A method of claim 28, wherein recording brain activity comprises recording evoked potential activity.

45. A method according to claim 28, wherein identifying comprises converting an analog record of brain activity to a digital record of brain activity.

46. The method of claim 45, further comprising using a hardware processor to control the time of onset of the plurality of auditory stimuli and to measure the change in brain activity of the one or more brain areas after presentation of the plurality of auditory stimuli.

47. The method of claim 46, wherein identifying comprises identifying one or more brain areas wherein broadband gamma waves of the one or more brain areas changes more after presentation of the speech sounds than it does after presentation of the non-speech sounds.

* * * * *